United States Patent
Okumura et al.

(10) Patent No.: US 11,156,552 B2
(45) Date of Patent: *Oct. 26, 2021

(54) PRISM, PRISM PRODUCTION METHOD, MOLD, AND SENSOR CHIP

(71) Applicant: KONICA MINOLTA, INC., Chiyoda-ku (JP)

(72) Inventors: Yoshihiro Okumura, Toyohashi (JP); Takehiko Goshima, Kunitachi (JP); Seiji Yuasa, Tama (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/514,223

(22) PCT Filed: Sep. 7, 2015

(86) PCT No.: PCT/JP2015/075316
§ 371 (c)(1),
(2) Date: Mar. 24, 2017

(87) PCT Pub. No.: WO2016/047427
PCT Pub. Date: Mar. 31, 2016

(65) Prior Publication Data
US 2017/0276604 A1 Sep. 28, 2017

(30) Foreign Application Priority Data
Sep. 24, 2014 (JP) .............................. JP2014-194253

(51) Int. Cl.
*G02B 5/04* (2006.01)
*G01N 21/552* (2014.01)
(Continued)

(52) U.S. Cl.
CPC ....... *G01N 21/553* (2013.01); *B29C 45/0025* (2013.01); *G01N 21/41* (2013.01);
(Continued)

(58) Field of Classification Search
CPC . G02B 5/00; G02B 5/008; G02B 5/04; G02B 5/045; G01N 21/41; G01N 21/553; G01N 21/64; G01N 21/6428
(Continued)

(56) References Cited

U.S. PATENT DOCUMENTS 5,661,303 A * 8/1997 Teder .................. G01N 21/43
250/227.25
5,907,408 A * 5/1999 Naya .................. G01N 21/211
356/445
(Continued)

FOREIGN PATENT DOCUMENTS

JP 2002-240107 8/2002
JP 2006-112808 4/2006
(Continued)

OTHER PUBLICATIONS

Search Report dated Mar. 29, 2018 which issued in the corresponding European Patent Application No. 15843536.2.
(Continued)

*Primary Examiner* — Thong Q Nguyen
(74) *Attorney, Agent, or Firm* — Cozen O'Connor

(57) ABSTRACT

A prism (1090) is configured from a dielectric medium and is used in analysis using surface plasmons. The prism (1090) is provided with an incidence surface (1170) on which excitation light from outside is incident, a reflection surface (1172) on which excitation light having entered the incidence surface (1170) is reflected, an emission surface (1174) from which excitation light reflected by the reflection surface (1172) is emitted, and an opposing surface (1175) opposing the reflection surface (1172). A gold film (1092) is formed on the reflection surface (1172). The opposing surface (1175) has a sink-mark surface (1200), and the sink-mark surface (1200) is a transparent surface.

12 Claims, 23 Drawing Sheets

(51) Int. Cl.
  *G01N 21/41* (2006.01)
  *G01N 21/64* (2006.01)
  *B29C 45/00* (2006.01)
  *G01N 33/543* (2006.01)
  *B29D 11/00* (2006.01)

(52) U.S. Cl.
  CPC ......... *G01N 21/64* (2013.01); *G01N 21/6428* (2013.01); *G01N 33/54373* (2013.01); *G02B 5/04* (2013.01); *B29D 11/0074* (2013.01); *G01N 2021/6439* (2013.01)

(58) Field of Classification Search
  USPC .................................................. 359/831–837
  See application file for complete search history.

(56) References Cited

U.S. PATENT DOCUMENTS

| | | | | |
|---|---|---|---|---|
| 6,627,910 | B2* | 9/2003 | Ishino | B60S 1/0822 |
| | | | | 250/227.29 |
| 6,700,716 | B2* | 3/2004 | Sejkora | F21V 5/02 |
| | | | | 216/24 |
| 8,354,644 | B2* | 1/2013 | Yasuda | G01N 21/552 |
| | | | | 250/341.1 |
| 9,435,919 | B2* | 9/2016 | Umetsu | G01N 21/648 |
| 9,464,988 | B2* | 10/2016 | Sando | G01N 33/54373 |
| 2002/0127706 | A1* | 9/2002 | Naya | G01N 21/553 |
| | | | | 435/287.2 |
| 2003/0184755 | A1* | 10/2003 | Mori | G01N 21/553 |
| | | | | 356/445 |
| 2004/0036881 | A1* | 2/2004 | Sharma | G01N 21/553 |
| | | | | 356/445 |
| 2006/0082779 | A1* | 4/2006 | Muraishi | B01L 3/502 |
| | | | | 356/445 |
| 2008/0074671 | A1* | 3/2008 | Ohtsuka | G01N 21/6428 |
| | | | | 356/455 |
| 2008/0094845 | A1* | 4/2008 | Kusano | F21V 5/02 |
| | | | | 362/339 |
| 2009/0009844 | A1* | 1/2009 | Kogo | G02B 26/125 |
| | | | | 359/216.1 |
| 2009/0230308 | A1* | 9/2009 | Kimura | G01N 21/47 |
| | | | | 250/363.01 |
| 2010/0128346 | A1* | 5/2010 | Achtner | G02B 25/001 |
| | | | | 359/482 |
| 2011/0181961 | A1 | 7/2011 | Imai | |
| 2012/0300306 | A1* | 11/2012 | Nagahama | E06B 9/386 |
| | | | | 359/601 |
| 2014/0043585 | A1* | 2/2014 | Wilson | G02B 1/14 |
| | | | | 351/159.57 |

FOREIGN PATENT DOCUMENTS

| | | |
|---|---|---|
| JP | 2006-264192 | 10/2006 |
| JP | 2007-071548 | 3/2007 |
| WO | WO2011/152064 * | 12/2011 |
| WO | WO 2013/027544 | 2/2013 |
| WO | WO 2013/146615 | 10/2013 |
| WO | WO 2014/109327 | 7/2014 |

OTHER PUBLICATIONS

International Preliminary Report on Patentability and Written Opinion dated Mar. 28, 2017 which issued in the corresponding International Patent Application No. PCT/JP2015/075316.

Office Action dated Oct. 2, 2018 issued in the corresponding Japanese Patent Application No. 2016-550089.

Office Action dated Aug. 10, 2021 issued in European Patent Application No. 15843536.2.

* cited by examiner

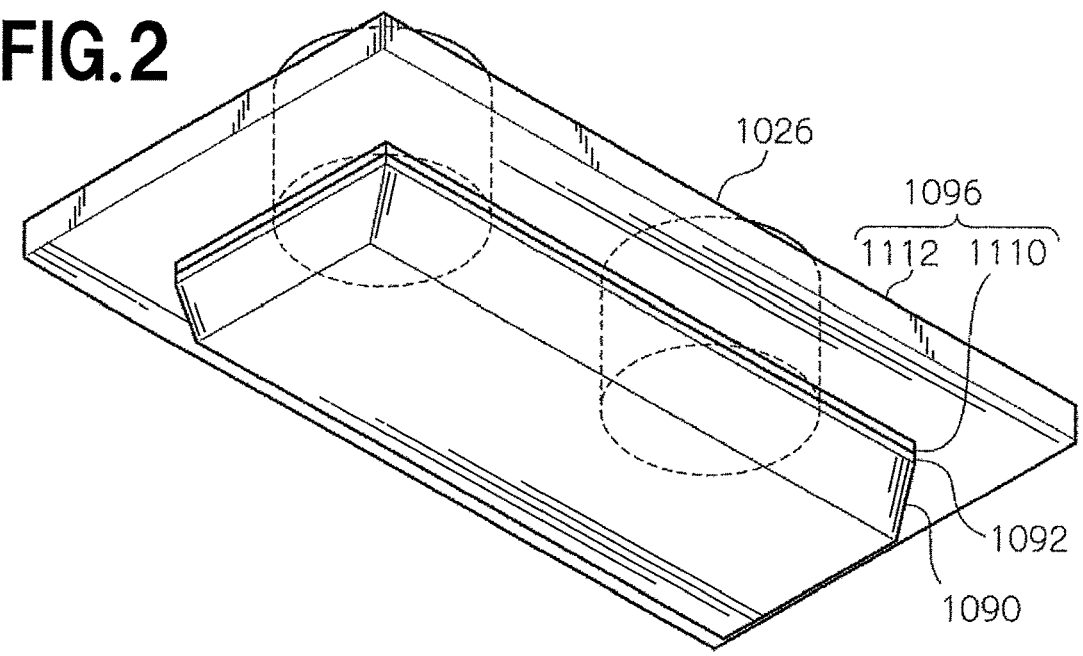
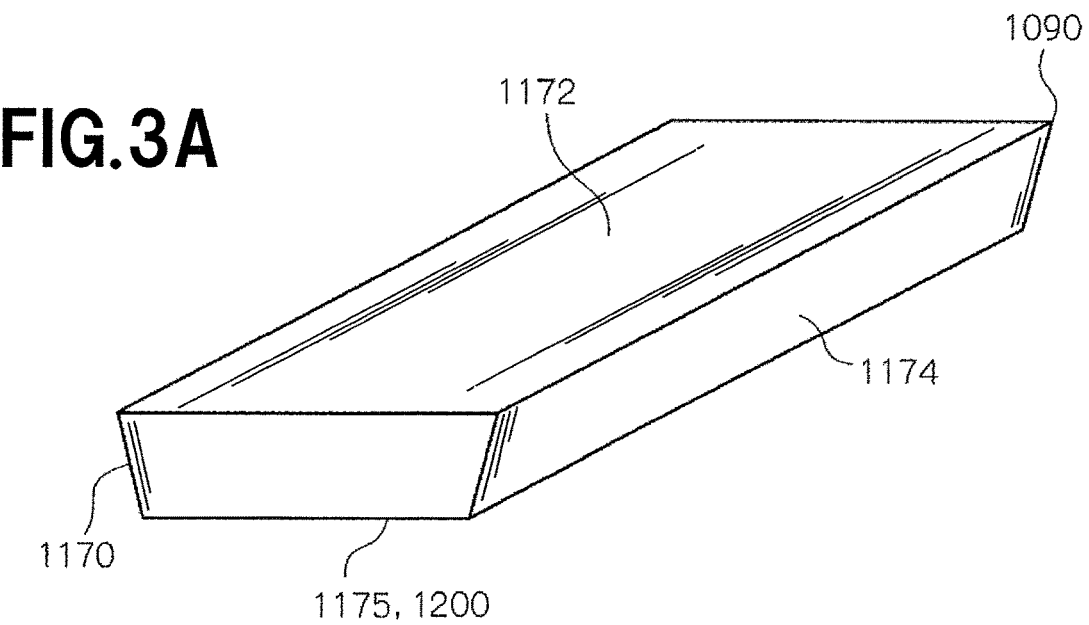
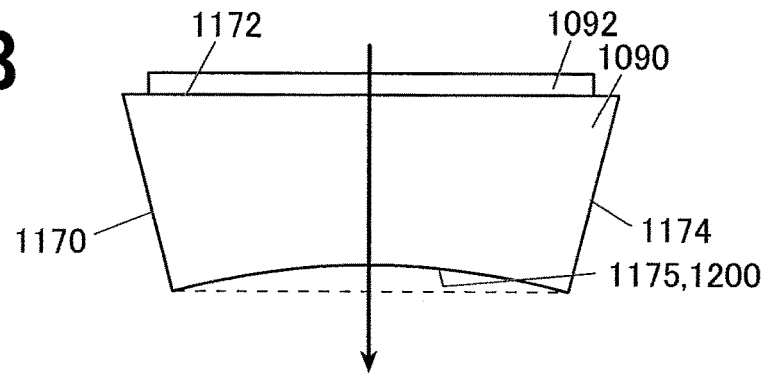

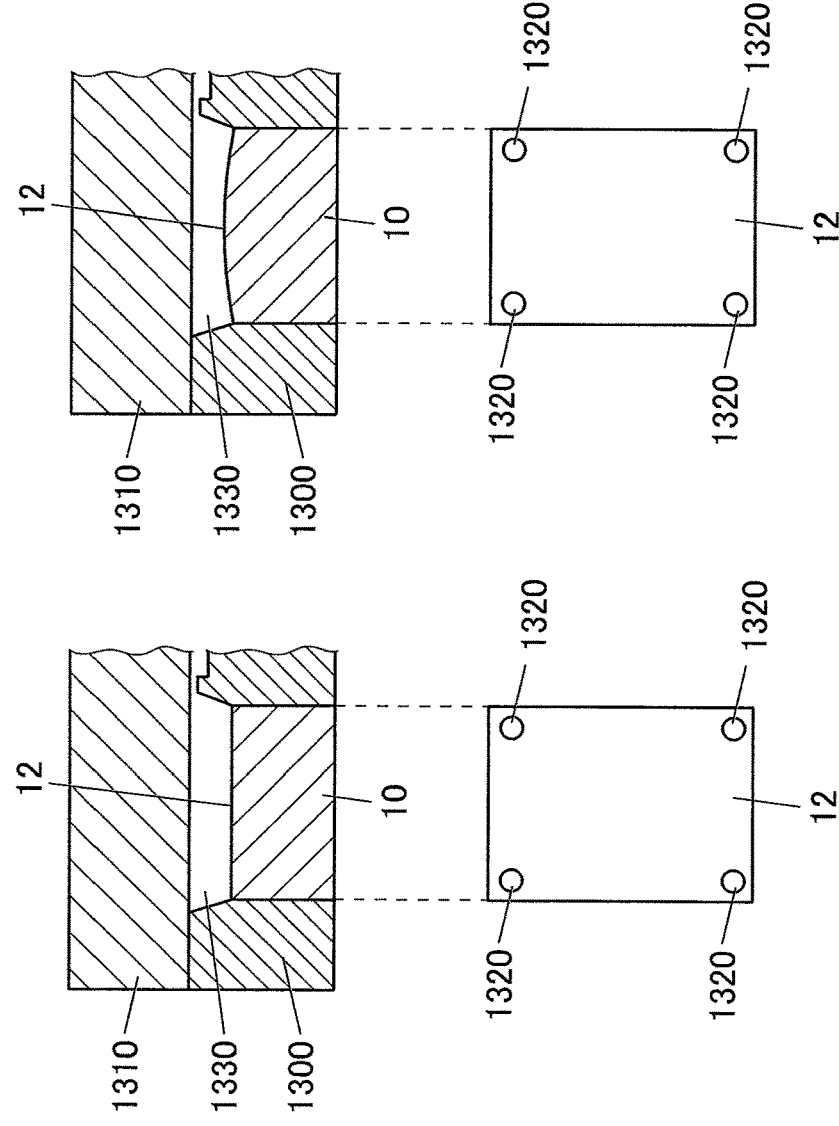

PRISM, PRISM PRODUCTION METHOD, MOLD, AND SENSOR CHIP

RELATED APPLICATIONS

This is a U.S. National Phase Application under 35 USC 371 of International Application PCT/JP2015/075316 filed on Sep. 7, 2015.

This application claims the priority of Japanese application no. 2014-194253 filed Sep. 24, 2014, the entire content of which is hereby incorporated by reference.

TECHNICAL FIELD

The present invention relates to a prism that is used for detecting a substance of interest in sample solution by utilizing SPR (surface plasmon resonance).

BACKGROUND ART

In a measurement of detecting biological substances such as protein and DNA (deoxyribonucleic acid), sensitive and quantitative detection of a minute amount of substance of interest enables immediately understanding the condition of a patient and initiating a treatment. For this purpose, analyzing techniques that can sensitively and quantitatively detect weak light caused by a minute amount of substance of interest has been required, and SPFS (surface plasmon-field enhanced fluorescence spectroscopy) has been known as one of such techniques.

A prism with a metal film on a predetermined surface thereof is used in the SPFS. By irradiating the metal film with excitation light via the prism from an angle at which surface plasmon resonance is induced, it is possible to produce local-field light (enhanced electric field) on the surface of the metal film. Since the local-field light excites a fluorescent substance that labels the substance of interest trapped on the metal film, it is possible to detect the presence or the amount of the substance of interest by detecting fluorescence emitted from the fluorescent substance.

Particularly in Patent Document 1, a concave sink-mark surface is formed in an opposing surface of a prism that is opposed to a reflection surface on which a metal film is formed, and it is intended to accumulate a sink mark in the sink-mark surface in resin molding. With this configuration, it is intended to maintain the polarization condition of the incident excitation light at a high level so as to improve the sensitivity and the accuracy of detection of a substance of interest (see paragraphs 0066 to 0067 and the like).

PRIOR ART DOCUMENT

Patent Document

Patent Document 1: WO 2013/146615A

However, in order to control the film thickness of the metal film in the technique of Patent Document 1, it is required to prepare a mock glass 200 with a metal film 100 for monitoring the film thickness (see FIG. 26) separately from the prism with the metal film and to perform alternative estimation (measurement of transmittance) by transmitting light through the mock. That is, in the technique of Patent Document 1, when light is transmitted through the prism with the metal film for measuring the film thickness of the metal film, the transmitted light may be diffused on the sink-mark surface, and it is therefore impossible to accurately figure out the actual film thickness of the metal film on the prism.

SUMMARY OF THE INVENTION

Therefore, it is a major object of the present invention to provide a prism which enables the film thickness of the metal film to be figured out accurately.

In order to achieve the object, the present invention is a prism which is constituted by a dielectric medium and is used for an analysis utilizing surface plasmon, including:

an incidence surface through which excitation light enters from an outside;

a reflection surface on which the excitation light which has entered through the incidence surface is reflected;

an emission surface through which the excitation light which has been reflected on the reflection surface exits; and an opposing surface which is opposed to the reflection surface, wherein a metal film is formed on the reflection surface, wherein the opposing surface comprises a sink-mark surface, and wherein the sink-mark surface is transparent.

Advantageous Effects of Invention

With the present invention, it is possible to provide a prism with uniform distribution of the polarization condition since an opposing surface has a sink-mark surface in which a sink mark is preferentially formed while it is also possible to figure out the accurate film thickness of a metal film since the transparent sink-mark surface prevents the transmitted light from being diffused thereon.

BRIEF DESCRIPTION OF DRAWINGS

FIG. 2 is a perspective appearance view of a sensor chip.

FIG. 3A is a perspective appearance view of a prism.

FIG. 3B is a side view of the prism.

FIG. 10B is a partial enlargement of the movable mold, in which the upper part is a cross sectional view and the lower part is a plan view of a transfer area for forming a sink-mark surface.

FIG. 10C illustrates a variation of FIG. 10B.

FIG. 10D illustrates a variation of FIG. 10B.

EMBODIMENTS FOR CARRYING OUT INVENTION

Hereinafter, preferred embodiments of the present invention will be described with reference to drawings.

First Embodiment

Figure 1:
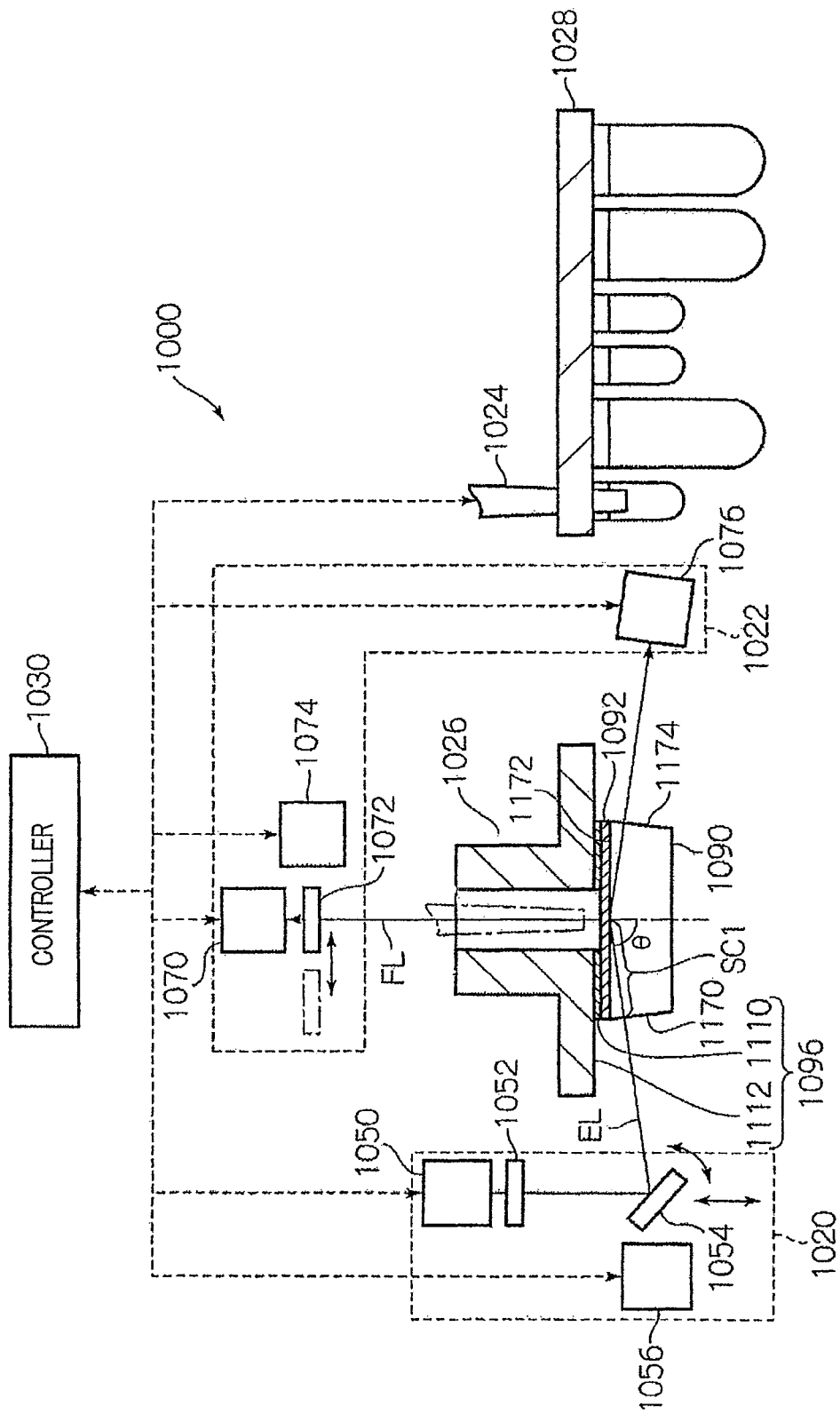
FIG. 1 is a schematic view of a measuring apparatus.

First, the schematic configuration and the components of a measuring apparatus 1000 including a prism will be described. The measuring apparatus 1000 performs measurement by chip surface plasmon-field enhanced fluorescence spectroscopy (SPFS). FIG. 1 is a schematic view of the overall configuration of the measuring apparatus.

Overall Configuration and Components of Measuring Apparatus

As illustrated in FIG. 1, the measuring apparatus 1000 includes an irradiating mechanism 1020, a measuring mechanism 1022, a fluid feeding mechanism 1024, a sensor chip 1026, a regent chip 1028 and a controller 1030. The irradiating mechanism 1020 includes a laser diode 1050, a linear polarizer plate 1052, a mirror 1054 and a mirror driving mechanism 1056. The measuring mechanism 1022 includes a photomultiplier tube 1070, a low-pass filter 1072, a low-pass filter moving mechanism 1074 and a photodiode 1076. The measuring apparatus 1000 may include additional components other than these components. Further, one or some of these components may be omitted from the measuring apparatus 1000.

Sensor Chip

As illustrated in FIG. 2, the sensor chip 1026 includes a prism 1090, a gold film 1092 and a channel forming body 1096.

The gold film 1092 is an example of a metal film, which can be made of other metals as well as gold. The material of the metal film is not particularly limited and may be any metal that can cause surface plasmon resonance. Examples of such materials of the metal film include gold, silver, copper, aluminum and the alloys thereof. The method of forming the metal film is not particularly limited. Examples of methods of forming the metal film include sputtering, vapor deposition and plating. The thickness of the metal film is not particularly limited but is preferably within the range of 30 nm to 70 nm.

The channel forming body 1096 includes a channel forming sheet 1110 and a channel forming lid 1112. A channel (not shown) is formed in the channel forming body 1096. The channel includes a supply path, a reaction chamber and a collection path. The reaction chamber is formed in the channel forming sheet 1110. The supply path and the collection path are formed in the channel forming lid 1112.

The sensor chip 1026 is also referred to as an "inspection chip", an "analysis chip", a "biochip", a "sample cell" or the like. The sensor chip 1026 is desirably a structural object with a length of each side within the range of several millimeters to several centimeters but may be replaced with a smaller or larger structural object that cannot be called as a "chip".

Prism

As illustrated in FIG. 3A, the prism 1090 is a dielectric medium made of a resin transparent to excitation light EL, which is in the shape of a trapezoidal pillar, desirably an isosceles trapezoidal pillar. The shape of the prism 1090 is determined so that excitation light EL can be incident on a reflection surface 1172 at an incident angle θ at which the electric field enhancement reaches the maximum. As long as this condition is met, the prism 1090 may be in other shapes as well as a trapezoidal pillar. Further, the prism 1090 may be replaced with an object that cannot be called as a "prism" in terms of the shape. For example, the prism 1090 may be in the shape of a semicircular pillar, or the prism 1090 may be replaced with a plate. The method of producing the prism 1090 will be described later.

As illustrated in FIG. 3A, the prism 1090 includes an incidence surface 1170, the reflection surface 1172, an emission surface 1174 and an opposing surface 1175. The incidence surface 1170 corresponds to one of the inclined side surfaces of the prism 1090, the reflection surface 1172 corresponds to the wider one of the parallel side surfaces of the prism 1090, the emission surface 1174 corresponds to the other inclined side surface of the prism 1090, and the entire opposing surface 1175 that is opposed to the reflection surface 1172 is a sink-mark surface 1200.

As illustrated in FIG. 3B, the sink-mark surface 1200 is a surface in which a sink mark is formed, which is a transparent and concave surface. As can be seen in FIG. 3B, the concavity of the concave sink-mark surface 1200 has an arcuate curvature that extends over the entire extent of the sink-mark surface 1200.

As used herein, the term "transparent" means optically transparent, i.e. the light transmittance is so high that the other side can be seen through the sink-mark surface 1200. In detail, the term means that the surface roughness Ra is from 0.1 nm to less than 0.5 μm. In more detail, the term means that a mold surface with a surface roughness Ra of from 0.1 nm to less than 0.5 μm is transferred (surface roughness Ra will be described later).

Figure 4:
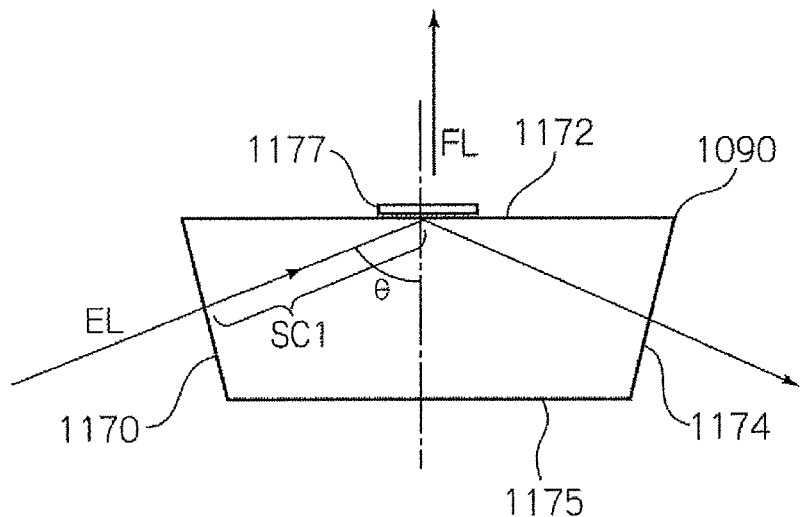
FIG. 4 is a vertical cross sectional view of the prism.

As illustrated in FIG. 4, the incidence surface 1170, the reflection surface 1172 and the emission surface 1174 of the prism 1090 are disposed such that the excitation light EL enters through the incidence surface 1170, is reflected on the reflection surface 1172 and exits through the emission surface 1174.

Hereinafter, resin materials that can be used as the material of the prism 1090 will be described with respect to the transparency, the resistance to fluid, the hardness, the water absorption, the refractive index, the photoelastic coefficient, the autofluorescence, the relationship between the maintenance ratio of a P-polarization component and sensitivity of SPR/SPFS measurement and the like.

Transparency

The resin material of the prism 1090 is transparent to the excitation light EL.

Resistance to Fluid

The prism 1090 is desirably resistant to organic solvent, acidic solution and basic solution. The resistance is evaluated by a test method according to JIS K7114. Examples of the organic solvent include ethanol, isopropylalcohol (IPA), acetone, N,N-dimetylformamide (DMF), dimethylsulfoxide (DMSO) and the like. The acidic solution refers to solution at a pH of from 4 to 7. The basic solution refers to solution at a pH of from 7 to 8.

Hardness of Prism

The hardness of prism 1090 is desirably equal to or less than H. This facilitates forming a mixture layer (electrically conductive body implanted layer) on the surface of the prism 1090, which improves the adhesion strength between an electrically conductive film and the prism. The hardness is evaluated by a test method according to JIS K5401.

Water Absorption of Prism

The water absorption of the prism 1090 is desirably equal to or less than 0.2%, more desirably equal to or less than 0.1%. This reduces the amount of water to be absorbed in the prism 1090 when the prism 1090 is immersed in fluid. The water absorption is evaluated by a test method according to JIS K7209. JIS K7209 defines test methods for the water absorption and the boiling-water absorption of plastics.

Refractive Index of Prism

The refractive index (n) of the prism 1090 is equal to or greater than 1.5.

Photoelastic Coefficient and P-Polarization Maintenance Ratio of Prism

Since the maintenance ratio of a P-polarization component decreases with an increase of the photoelastic coefficient of the prism 1090, the photoelastic coefficient of the resin material of the prism 1090 is desirably equal to or less than $80 \times 10^{-12}$ $Pa^{-1}$. Further, the prism 1090 is produced from a resin material that exhibits a phase difference of 153 nm or less, desirably 46 nm or less in the vicinity of a gate of a test piece with a dimension of diameter ($\varphi$) 11 mm and thickness t=3 mm, which is evaluated by the Senarmont method using light at a wavelength of 550 nm. This increases the light intensity of a P-polarization component that is incident on the reflection surface 1172 of the prism 1090 even when the density of the prism 1090 is uneven in the inner portion. An increase of the light intensity of a P-polarization component that is incident on the reflection surface 1172 of the prism 1090 increases the light intensity of the surface plasmon-excited fluorescence FL, which improves the sensitivity and the accuracy of measurement.

Autofluorescence

When a sample is fed in the amount of the lower detection limit in an SPFS analysis, the light intensity of the autofluorescence is less than the light intensity of the surface plasmon-excited fluorescence FL emitted from the sample. As used herein, the amount of sample means the amount of antigen. Specifically, the lower detection limit of the antigen is a small value, for example, like 0.25 mol.

Polarization Maintenance Ratio and Distribution of Polarization Condition in Prism The maintenance ratio of the P-polarization component of P-polarized light that has entered the prism is equal to or greater than 90%, preferably within the detection range of 98±2% in a section from the incidence surface to the reflection surface. This enables transmitting the energy of an evanescent wave caused by surface plasmon resonance to a sample without loss, which improves the sensitivity and the accuracy of SPR/SPFS measurement.

Measuring Method of P-Polarization Maintenance Ratio

Figure 5:
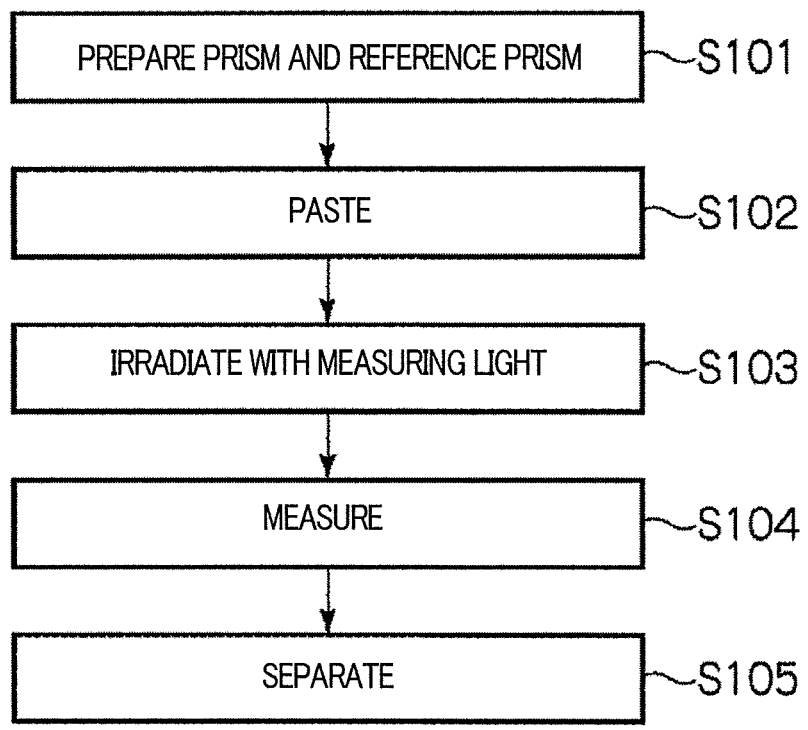
FIG. 5 is a flowchart of the process of measuring the P-polarization component maintenance ratio of a prism.

A measuring method for P-polarization maintenance ratio will be described referring to FIG. 5. The flowchart of FIG. 5 illustrates the process of measuring the maintenance ratio of the P-polarization component in the section from the incidence surface to the reflection surface of the prism 1090. The schematic view of FIG. 6 depicts a measuring apparatus for measuring the maintenance ratio of a P-polarization component in the section from the incidence surface to the reflection surface of the prism 1090.

Figure 6:
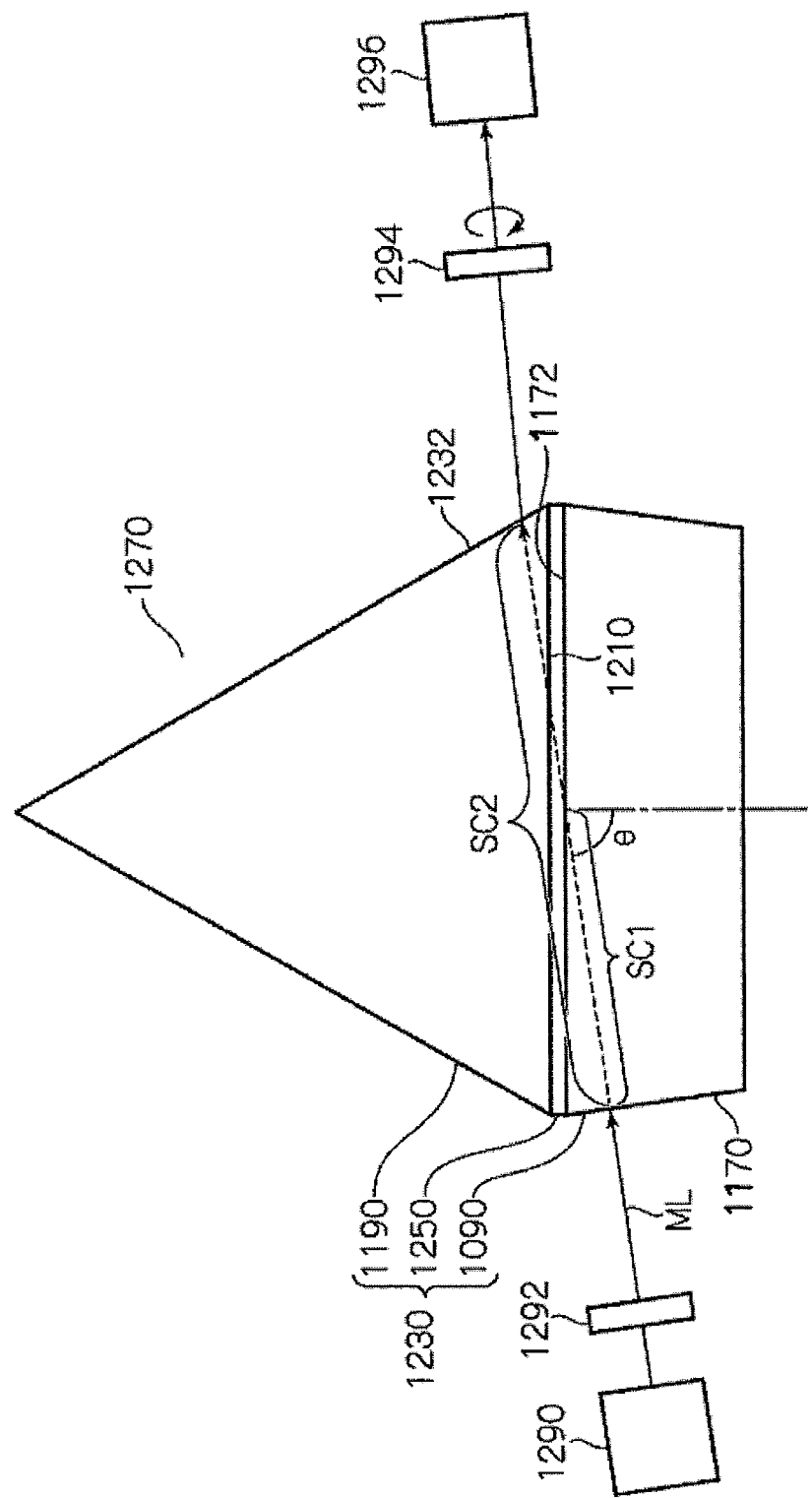
FIG. 6 is a measuring apparatus for the P-polarization component maintenance ratio of a prism.

To measure the maintenance ratio of a P-polarization component in the section SC1, the prism 1090 and a reference prism 1190 are prepared as illustrated in FIG. 5 and FIG. 6 (Step S101). The reference prism 1190 is made of a material that is transparent to the excitation light EL and does not cause birefringence. For example, the reference prism 1190 is made of glass such as BK7. Desirably, the refractive index of the prism 1090 is equal to the refractive index of the reference prism 1190. This prevents refraction and reflection of light on the interface between the prism 1090 and the reference prism 1190 and thus enables the maintenance ratio of the P-polarization component in the section SC1 to be readily measured. However, even when the refractive index of the prism 1090 is not equal to the refractive index of the reference prism 1190, it is still possible to measure the maintenance ratio of a P-polarization component in the section SC1.

After the prism 1090 and the reference prism 1190 are prepared, the reflection surface 1172 of the prism 1090 is pasted on an incidence surface 1210 of the reference prism 1190 (Step S102). An assembly 1230 of the prism 1090 and the reference prism 1190 is thus prepared. In the pasting step, a matching oil 1250 is desirably intervened between the reflection surface 1172 of the prism 1090 and the incidence surface 1210 of the reference prism 1190. This reduces the gap between the reflection surface 1172 of the prism 1090 and the incidence surface 1210 of the reference prism 1190 and thereby reduces diffusion of measuring light ML between the reflection surface 1172 of the prism 1090 and the incidence surface 1210 of the reference prism 1190, which enables the maintenance ratio of the P-polarization component in the section SC1 to be readily measured. When the contact between the reflection surface 1172 of the prism 1090 and the incidence surface 1210 of the reference prism 1190 is fine, the matching oil 1250 may be omitted.

After the assembly 1230 is prepared, the assembly 1230 is installed in a measuring apparatus 1270, and the assembly 1230 is irradiated with the measuring light ML (Step S103). The measuring light ML enters through the incidence surface 1170 to the prism 1090, passes through the reflection surface 1172 of the prism 1090 and the incidence surface 1210 of the reference prism 1190 and exits through the emission surface 1232 from the reference prism 1190. The measuring light ML is emitted from a laser diode 1290, passes through a polarization rotator 1292 and is incident on the incidence surface 1170 of the prism 1090. Desirably, the wavelength, the light intensity and the incident angle θ of the measuring light ML are respectively equal to the wavelength, the light intensity and the incident angle θ of the excitation light EL. In this case, the maintenance ratio of a P-polarization component in the section SC is measured in the same condition as in measuring the light intensity of surface plasmon-excited fluorescence FL. The measuring light ML is linearly polarized light that is adjusted to the same polarization direction as the P-polarized light on the reflection surface 1172 of the prism 1090 by means of the fixed polarization rotator 1292. The laser diode 1290, which is a He—Ne laser that emits light at a wavelength of 632 nm for example, emits a beam having a cross-sectional diameter of 1 mm.

While the assembly 1230 is being irradiated with the measuring light ML, the maintenance ratio of the P-polarization component is measured in a section SC2 between the incidence surface 1170 of the prism 1090 and the emission surface 1232 of the reference prism 1190 (Step S104).

Since the reference prism 1190 does not cause birefringence, the maintenance ratio of the P-polarization component in the section SC2 is considered to be equal to the maintenance ratio of the P-polarization component in the section SC1.

In the measuring apparatus 1270, the measuring light ML that has exited through the emission surface 1232 of the reference prism 1190 passes through a polarization rotator 1294 to reach a power meter 1296. The polarization rotator 1294 spins around the optical axis up to 180° in increments of 15°, and the light intensity of the measuring light ML is measured by means of the power meter 1296. In this way, the maintenance ratio of the P-polarization component in the section SC1 is measured. However, the maintenance ratio of a P-polarization component in the section SC1 may be measured by other methods.

After the maintenance ratio of the P-polarization component in the section SC1 is measured, the prism 1090 and the reference prism 1190 are separated from each other (Step S105).

Measurement of Autofluorescence

To measure the light intensity of the autofluorescence, a Raman spectrometer is prepared and the fluorescence spectrum is measured. The prism 1090 is irradiated with a laser beam at the same wavelength as the excitation light EL. When the prism 1090 is irradiated with a laser beam at a wavelength of 632 nm, a filter that attenuates light at a wavelength of 650 nm or less is used for measuring the light intensity of the autofluorescence.

Specific Example of Resin

The resin of the prism 1090 is preferably a cycloolefin polymer, more desirably ZEONEX_E48R of Zeon Coporation (trade name, hereinafter referred simply as "E48R"). The refractive index of E48R is 1.51 at a wavelength of 632 nm. E48R is advantageous in emitting weak autofluorescence.

Figure 7:
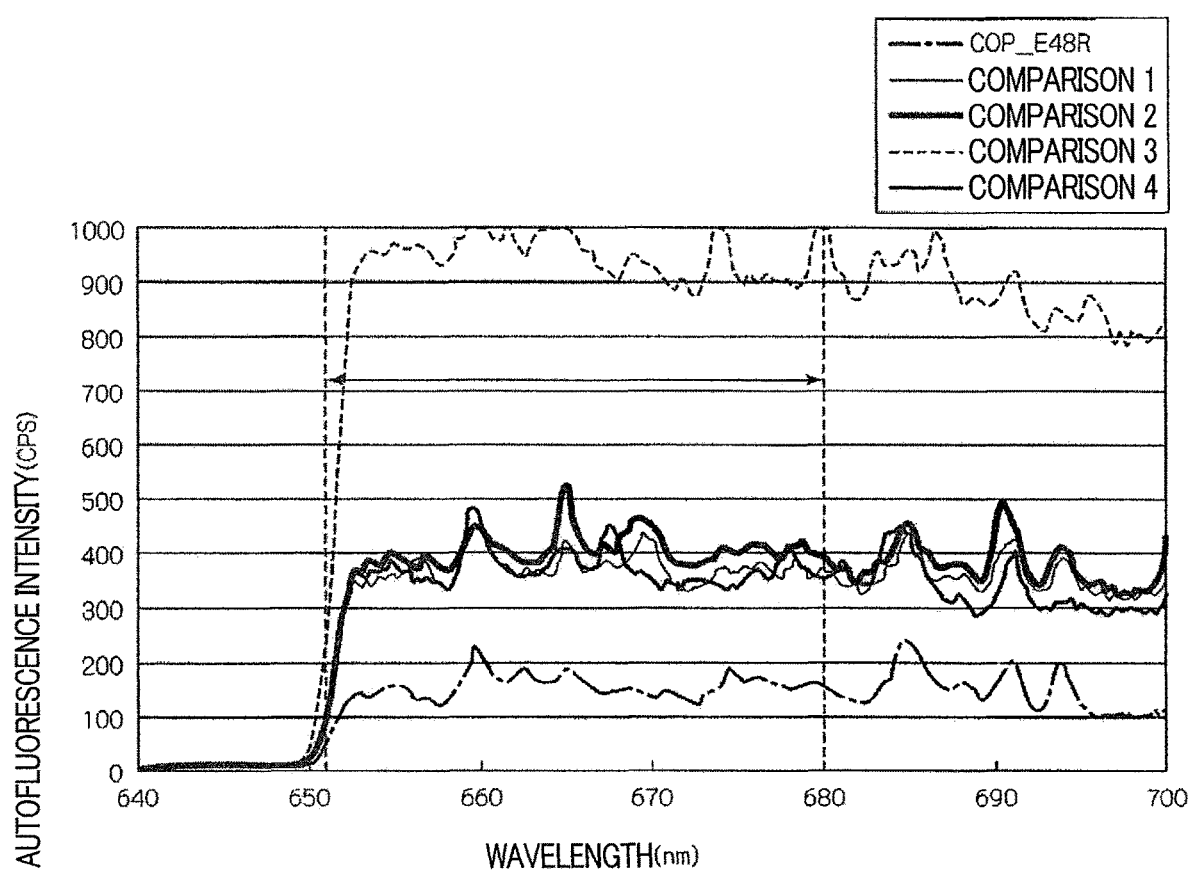
FIG. 7 is a graph of autofluorescence spectrum.

The graph of FIG. 7 shows autofluorescence spectrum. The autofluorescence spectrum of E48R and resins for comparison, "Comparison 1", "Comparison 2", "Comparison 3" and "Comparison 4", is shown in FIG. 7. When the wavelength of the excitation light is 632 nm, the light intensity of the autofluorescence emitted from E48R is remarkably less than that emitted from the resins for comparison in the wavelength range of 650 nm to 680 nm, which is the wavelength range to be measured of the surface plasmon-excited fluorescence FL (light receiving and detecting range, the zone indicated by the arrow in FIG. 7). Accordingly, E48R exhibits remarkably weak integrated intensity of the autofluorescence in the wavelength range to be measured, which is less than 5000 cps even including the deviation. Accordingly, the light intensity of the autofluorescence is less than the light intensity of the surface plasmon-excited fluorescence FL.

Hardness when Electrically Conductive Film is Gold Film

Figure 8:
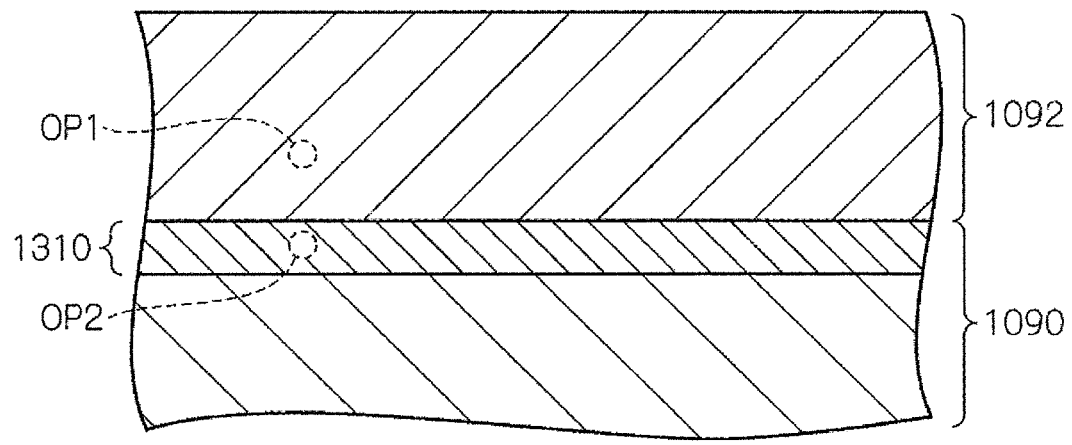
FIG. 8 is a cross sectional view around the boundary between a gold film and a prism.
Figure 9:
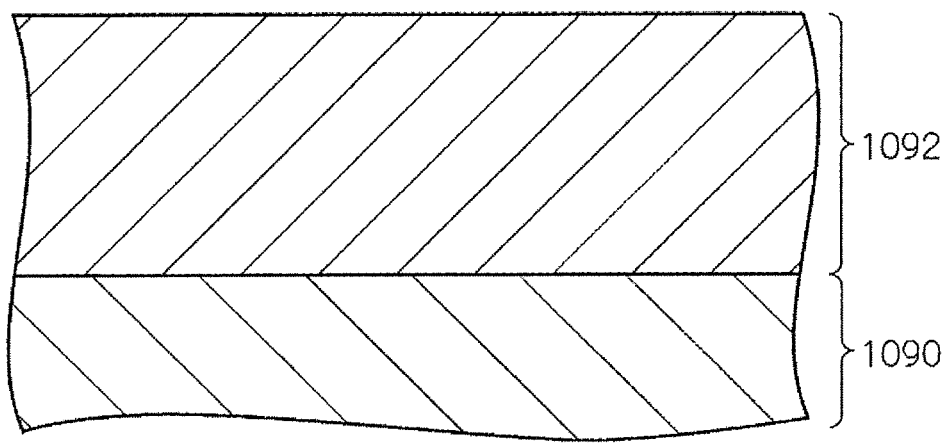
FIG. 9 is a cross sectional view around the boundary between the gold film and the prism.

The case in which a gold film with a film thickness of from 40 nm to 50 nm is provided. The schematic views of FIG. 8 and FIG. 9 are cross sectional views around the boundary between the gold film and the prism. FIG. 8 illustrates a case in which the hardness of the prism is equal to or less than H. FIG. 9 illustrates a case in which the hardness of the prism is greater than H. When the hardness is equal to or less than H, e.g. when the prism 1090 is made of ZEONEX_E48R (trade name) of Zeon Corporation (Chiyoda-ku, Tokyo) and has a hardness of H, a mixture layer 1310 with a layer thickness of from 2 nm to nm is formed on the surface of the prism 1090 as illustrated in FIG. 8. An observation of a cross section under a focused ion beam transmission electron microscope (FIB-TEM) confirmed that gold is contained not only in an observation field OP1 in the cross section of the gold film 1092 but also in an observation field OP2 in the cross section of the mixture layer 1310.

When the hardness is greater than H, e.g. when the prism 1090 is made of ZEONEX_330R (trade name) of Zeon Corporation and has a hardness of 3H, a mixture layer 1310 was not formed as illustrated in FIG. 9, and sufficient film adhesion was not achieved.

Measurement

Prior to a measurement using the measuring apparatus, an antigen is bound to an antibody (hereinafter referred to as an "immobilized antibody") that is immobilized on an antigen trapping membrane (not shown) by immune reaction (antigen-antibody reaction), so that the antigen is trapped on the antigen trapping membrane. Subsequently, an antibody that functions as fluorescent labeling (hereinafter referred to as a "fluorescent-labeling antibody") is bound to the antigen by immune reaction, so that fluorescent labeling is attached to the antigen trapped on the antigen trapping membrane.

To carry out the measurement, the prism 1090 is irradiated with the excitation light EL by means of the irradiating mechanism 1020 as illustrated in FIG. 1. As illustrated in FIG. 4, the excitation light EL directed to the prism 1090 travels inside the prism 1090, is reflected on the reflection surface 1172 (in more detail, the interface between the prism 1090 and the gold film 1092) and exits through the emission surface 1174. While the prism 1090 is being irradiated with the excitation light EL, evanescent light oozes from the interface between the prism 1090 and the gold film 1092 toward the gold film 1092, and the evanescent wave resonates with the surface plasmon of the gold film 1092, which enhances the electric field of the evanescent wave. The incident angle θ of the excitation light EL on the interface between the prism 1090 and the gold film 1092 is selected so that the enhancement of the electric field of the evanescent wave reaches the maximum. The enhanced electric field acts on the fluorescent labeling so that the surface plasmon-excited fluorescence FL is emitted from the antigen trapping membrane. The light intensity of the surface plasmon-excited fluorescence FL is measured by means of the photomultiplier tube 1070. The measurement result is sent to a controller 1030 where the interaction between the immobilized antibody and the antigen is detected, so that the presence of the antigen, the amount of antigen and the like are determined.

Fluid Feeding Mechanism

Back to FIG. 1, the fluid feeding mechanism 1024 supplies fluids such as sample solution, fluorescent labeling solution and buffer solution to the sensor chip 1026 and collects fluids such as the sample solution, the fluorescent labeling solution and buffer solution from the sensor chip 1026. When the fluids are supplied to the sensor chip 1026, each fluid is supplied to a supply opening, and the reaction chamber is filled with the fluid, so that the fluid comes in contact with the antigen trapping membrane.

In the fluid feeding mechanism 1024, for example, fluid is suctioned from a fluid source by means of a pump, the pump sends the fluid from the fluid source to the fluid destination, and the fluid is ejected to the fluid destination by means of the pump. Fluid may flow in a pipe from the fluid source to the fluid destination.

Sample Solution and Fluorescent Labeling Solution

The sample solution is typically a sample collected from human such as blood. However, it may be a sample collected from a living organism other than human or from non-living organism. Pretreatment such as dilution, blood cell separation and mixing with a regent may be given to the collected sample.

The fluorescent labeling solution contains a fluorescence-labeled antibody that binds to the antigen to be measured to serve as fluorescent labeling. The fluorescence-labeled antibody has a chemical structure that emits fluorescence to serve as a fluorescent labeling.

Laser Diode

As illustrated in FIG. 1, the laser diode 1050 emits the excitation light EL. The laser diode 1050 may be replaced with another type of light source. For example, the laser diode 1050 may be replaced with a light emitting diode, a mercury lamp, a laser device other than a laser diode, or the like.

When the light emitted from the light source is not a parallel beam, it is converted to a parallel beam by means of a lens, a mirror, a slit or the like. When the light is not linearly polarized, it is converted to linear polarized light by means of a linear polarizer plate or the like. When the light is not monochromatic, it is converted to monochromatic light by means of a diffracting grating or the like.

Linear Polarizer Plate

As illustrated in FIG. 1, the linear polarizer plate 1052 is disposed in the optical path of the excitation light EL so as to convert the excitation light EL emitted from the laser diode 1050 to linearly polarized light. The polarization direction of the excitation light EL is selected so that the excitation light EL is P-polarized with respect to the reflection surface 1172 of the prism 1090. This increases the amount of evanescent wave oozed and thus increases the light intensity of the surface plasmon-excited fluorescence, which improves the sensitivity and the accuracy of measurement.

Mirror and Mirror Driving Mechanism

As illustrated in FIG. 1, the mirror 1054 is disposed in the optical path of the excitation light EL. The excitation light EL that has passed through the linear polarizer plate 1052 is reflected on the mirror 1054, and the prism 1090 is then irradiated with the excitation light EL. The light that is directed to the prism 1090 enters through the incidence surface 1170, is reflected on the reflection surface 1172 and exits through the emission surface 1174. The incident angle θ of the excitation light EL on the reflection surface 1172 satisfies a total reflection condition of $\theta c \leq \theta$ (where θc is the critical angle).

The mirror driving mechanism 1056, which includes a driving power source such as a motor or a piezoelectric actuator, rotates the mirror 1054 so as to adjust the position of the mirror 1054. Further, the mirror driving mechanism 1056, which includes a driving power source such as a linear stepping motor, moves the mirror 1054 along the optical axis of the laser diode 1050 so as to adjust the location of the mirror 1054. This enables adjusting the incident angle θ of the excitation light EL on the reflection surface 1172 of the prism 1090 while maintaining the incident location of the excitation light EL in the backside of the area in the reflection surface 1172 of the prism 1090 where the antigen trapping membrane is attached.

Photomultiplier Tube

As illustrated in FIG. 1, the photomultiplier tube 1070 is disposed in the optical path of the surface plasmon-excited fluorescence FL so as to measure the light intensity of the surface plasmon-excited fluorescence FL. The photomultiplier tube 1070 may be replaced with a different type of light intensity sensor. For example, the photomultiplier tube 1070 may be replaced with a charge coupled device (CCD) sensor or the like.

Low-Pass Filter

The low-pass filter 1072 transmits light at a wavelength of longer than the cut-off wavelength and attenuates light at a wavelength of shorter than the cut-off wavelength. The cut-off wavelength is selected within the range between the wavelength of the excitation light EL and the wavelength of the surface plasmon-excited fluorescence FL.

When the low-pass filter 1072 is disposed in the optical path of the surface plasmon-excited fluorescence FL, the low-pass filter 1072 attenuates the diffused excitation light EL so that only a fraction of the diffused excitation light EL reaches the photomultiplier tube 1070. In contrast, the low-pass filter 1072 transmits the surface plasmon-excited fluorescence FL so that most of the surface plasmon-excited light FL reaches the photomultiplier tube 1070. When the surface plasmon-excited fluorescence FL to be measured is comparatively weak, this reduces the influence of the comparatively strong diffused excitation light EL, which improves the accuracy of measurement. The low-pass filter 1072 may be replaced with a band-pass filter.

Low-Pass Filter Driving Mechanism

As illustrated in FIG. 1, the low-pass filter driving mechanism 1074 switches the state between a state in which the low-pass filter 1072 is disposed in the optical path of the surface plasmon-excited fluorescence FL and a state in which the low-pass filter 1072 is not disposed in the light path of the surface plasmon-excited fluorescence FL.

Photodiode

As illustrated in FIG. 1, the photodiode 1076 is disposed in the optical path of the excitation light EL that has been reflected on the interface between the prism 1090 and the gold film 1092, so as to measure the light intensity of the excitation light EL that has been reflected on the interface between the prism 1090 and the gold film 1092. The photodiode 1076 may be replaced with a different type of light intensity sensor. For example, the photodiode 1076 may be replaced with a phototransistor, a photoresistor or the like.

Controller

The controller 1030 is a built-in computer that executes a control program. A single built-in computer may function as the controller 1030, or two or more built-in computers may together function as the controller 1030. A hardware that is not associated with a software may have all or a part of the function of the controller 1030. Examples of such hardware include electronic circuits such as operational amplifiers and comparators. All of a part of the processing in the controller 1030 may be performed manually or outside the measuring apparatus 1000.

Production Method of Prism

Mold

Figure 10A:
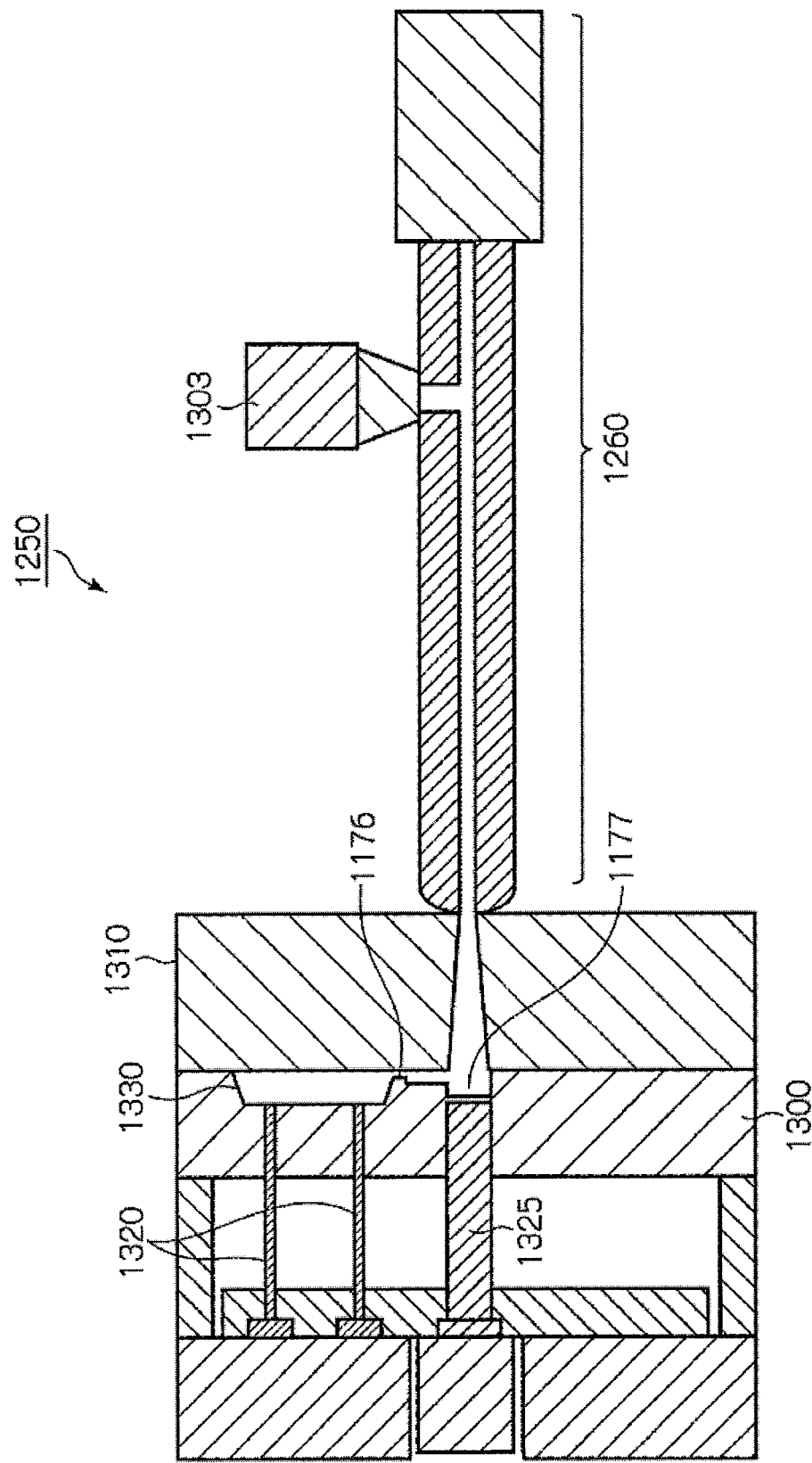
FIG. 10A is a schematic view illustrating a so-called mold closing step of butting a movable mold with a fixed mold to form a cavity.
Figure 11:
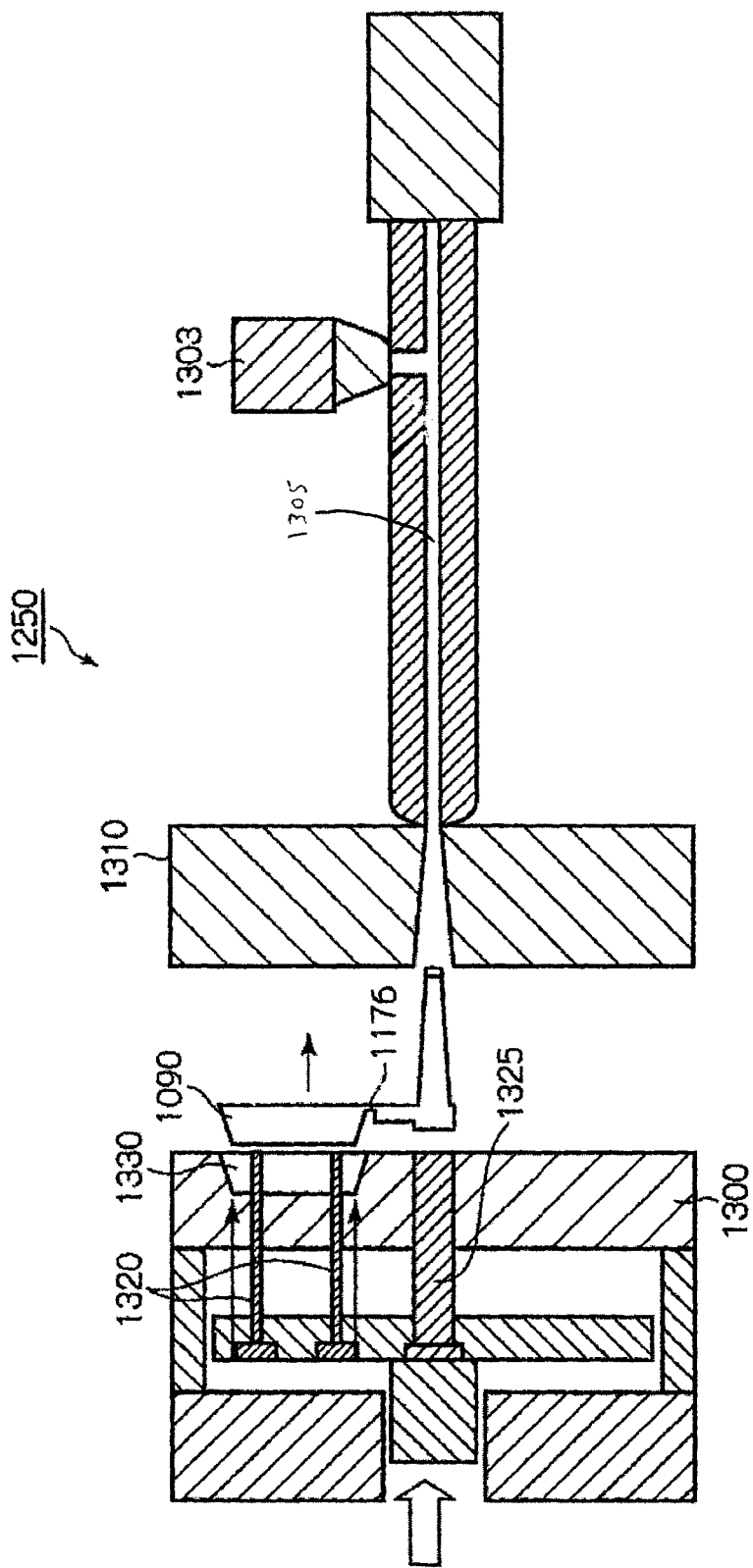
FIG. 11 is a schematic view illustrating a so-called ejecting step of releasing a prism from an injection molding machine.

The prism 1090 is completed through a predetermined process by using an injection molding machine. Hereafter, the injection molding process using an injection-molding mold will be briefly described with reference to FIG. 10 and FIG. 11. FIG. 10A is a schematic view illustrating a so-called mold closing step of butting a movable mold with a fixed mold to form a cavity. FIG. 11 is a schematic view illustrating a so-called ejecting step of releasing a prism from the injection molding machine.

As illustrated in FIG. 10A, an injection-molding mold 1250 includes a movable mold 1300 with a recess (cavity) 1330 in the shape of an injection-molded product, a fixed mold 1310 having a function of abutting the movable mold 1300 to close the recess 1330, ejector pins 1320, an ejector member 1325 and a cylinder portion 1260 that supplies resin material of the injection-molded product to the cavity.

As illustrated in FIG. 10B, the movable mold 1300 has a nest structure which includes a core 10. In the part of the core 10 that is exposed to the cavity, a transfer area 12 for forming a sink-mark surface 1200 is formed. In FIG. 10B, the ejector pins 1320 are provided at the four corners of the core 10.

In the configuration in FIG. 10B, the transfer area 12 has a flat surface, and the sink-mark surface 1200 that is formed by transferring the transfer area 12 is likely to has a concave surface. When the transfer area 12 has a flat surface, it is easier to process the mold surface (transfer area 12) and thus to adjust the surface roughness Ra of the transfer area 12 within the range of 0.1 nm to less than 0.5 μm. Accordingly, it is possible to form the transparent sink-mark surface 1200.

As illustrated in FIG. 10C, the transfer area 12 of the core 10 may preliminary have a convex surface. Further, as illustrated in FIG. 10D, the transfer area 12 of the core 10 may have a concave surface. Particularly with the configuration in FIG. 10D, it is possible to form the sink-mark surface 1200 into an approximately flat shape when a sink mark is caused in the sink-mark surface 1200 in resin molding. This enables the light transmittance to be readily measured.

Heat Conductivity (W·m/K)

The heat conductivity in the transfer area 12 of the core 10 is preferably from 0.6 W·m/K to 50 W·m/K, more preferably from 0.6 W·m/K to 20 W·m/K.

Examples of mold materials that allow the heat conductivity in the transfer area 12 of the core 10 to fall within the preferred range include a SUS material pasted or coated with a heat insulating resin, a SUS material with a ceramic layer that is pasted thereto or laminated thereon by thermal spraying, a SUS material with a Ni—P plating laminated thereon, a titanium alloy, chromium alloy-based stainless steels such as STAVAX, prehardened steels such as HPM38 and NAK, carbon steel and the like.

The "heat insulating resin" refers to a coating of polyimide, which is highly resistant to heat and chemical regents, or a film composed of a polyimide base and a heat resistant silicone adhesive applied thereon. The "STAVAX" is a chromium alloy-based stainless steel that is particularly resistant to corrosion and abrasion. The STAVAX has a recommended HRC of approximately from 45 to 54, a density at ordinary temperature of 7800 kg/m$^3$ and a specific heat of 460 J/(kg·k), and contains Cr (chromium), V (vanadium), Mn (manganese), Si (silicon), C (carbon) and the like.

Volume of Mold Material in Transfer Area for Forming Sink Mark

It is desirable that the thickness in the transfer area 12 of the core 10 is as thin as possible in order to avoid uneven cooling and to achieve stable and uniform distribution of birefringence. It should be understood well that the thickness is suitably adjusted according to the required specification of the prism 1090. For example, the configuration may be such that the base material is STAVAX, the entire surface of the transfer area 12 is uniformly plated with a low-heat conductive material, the transfer area 12 is lapped, and the end parts of the transfer area 12 are blasted so that the surface roughness Ra is greater in the end parts. Such configuration can induce a sink mark to be formed in the sink-mark surface 1200 and also reduce the influence of cracking on the optical surfaces (incidence surface 1170 and emission surface 1174) due to the blasted end parts with higher transferring property.

Surface Roughness Ra

The surface roughness Ra in the transfer area 12 of the core 10 is preferably from 0.1 nm to less than 0.5 μm. The term "surface roughness Ra" represents arithmetic average roughness Ra according to JIS B 0601: 2013. Arithmetic average roughness Ra is principally the arithmetic average of absolute values of deviation from the average line to a measured curve in a zone that is extracted from the roughness curve and has a reference length in the direction of the average line. In arithmetic average roughness Ra, a single scratch (unevenness) has a very small influence on a measured value, and it is therefore possible to obtain a stable result.

For example, when the surface roughness Ra in the transfer area 12 of the core 10 is 0.1 nm, the surface is a so-called mirror surface that is finished by polishing, grinding or the like. A surface having a surface roughness Ra of less than 0.5 μm can be obtained by grinding and subsequent blasting with small particles that is also known as IEPCO processing.

Injection Molding

An injection molding process involves a mold closing step, an injecting step, a dwell pressure applying step, a cooling step, a mold opening step and an ejecting/product collecting step, which are performed in the written order. In the mold closing step, the movable mold 1300 is butted with the fixed mold 1310 as illustrated in FIG. 10A so that the recess 1330 of the movable mold 1300 is closed to form a cavity. Then, a resin material (molten resin) 1305 from a resin material feeding furnace 1303 is injected so that the cavity is filled with the resin (injecting step). The resin material flows through a sprue 1177 and a gate 1176 to fill the cavity. When the resin material fills the cavity of the mold, it is cooled by the mold and shrinks. Since the shrinkage results in a change of the volume, the shrinkage can cause a dimensional change of a molded product, a failure in transferring a shape or the like. To avoid them, a dwell pressure is applied from the molding machine to make up for the loss of the resin due to the shrinkage (dwell pressure applying step). Then, the resin is cooled down in the mold to a temperature at which the product can be collected from the mold (cooling step).

Then, after a predetermined period of time is elapsed so that the resin material 1305 is sufficiently cooled down, the movable mold 1300 is separated from the fixed mold 1310 as illustrated in FIG. 11 (mold opening step). In this step, the molded product is attached to the movable mold 1300. Then, by sliding the ejector pins 1320 toward the fixed mold 1310, the prism 1090 is released (ejecting step). The prism 1090 is joined with a substrate and a channel forming part (not shown), and the sensor chip 1026 is thus obtained.

The sink mark in the opposing surface 1175 of the prism 1090 is formed in the above-described dwell pressure applying step. The sink mark is formed in the opposing surface 1175 at a dwell pressure of 65 MPa or less. In the ejecting step, ejector pin marks are typically formed in an injection-molded product. In the present prism 1090, ejector pin marks 1180 are formed in the opposing surface 1175 corresponding to the position of the ejector pins 1320.

Relationship Between Sink Mark and Polarization Maintenance Ratio

The application of a dwell pressure increases the internal stress of the prism 1090 which is a molded product, and the internal stress degrades the maintenance ratio of polarization condition of the prism 1090. It was found that the polarization maintenance ratio of the prism 1090 can be improved by setting the dwell pressure to such a low level that causes a sink mark in the prism 1090 so as to reduce the internal stress acting in the prism 1090.

Relationship Between Gate Position and Sink Mark

The gate 1176, which is an inlet opening through which the resin material flows into the mold, has a bridging function of filling the cavity with the resin material that flows in through the sprue 1177. The gate width GW is equal to or less than 40% of the short side length of the reflection surface 1172, and the gate thickness t2 is equal to or less than ½ of the thickness t1 of the prism (see FIG. 12A).

The prism 1090 is formed such that the gate 1176 (gate position) is located between the center C of the prism 1090 and the reflection surface 1172 with respect to the thickness direction of the prism 1090. That is, in the example of FIG. 12A, it is required to form the gate 1176 inside the gate position area W.

Figure 12A:
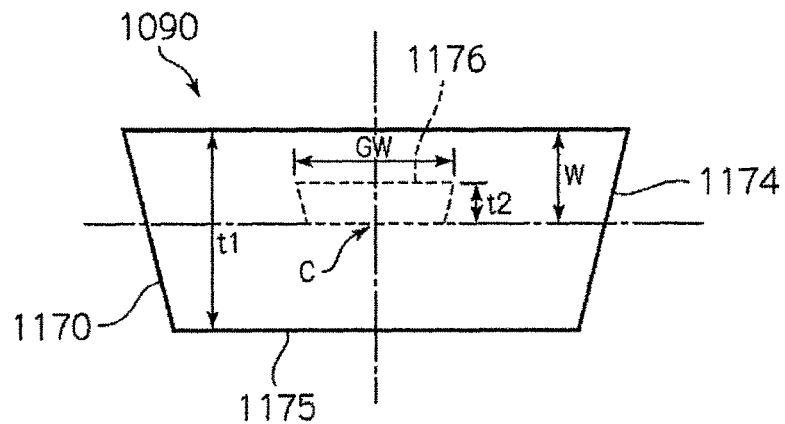
FIG. 12A illustrates an example of the relationship between the gate position and a sink mark.
Figure 12B:
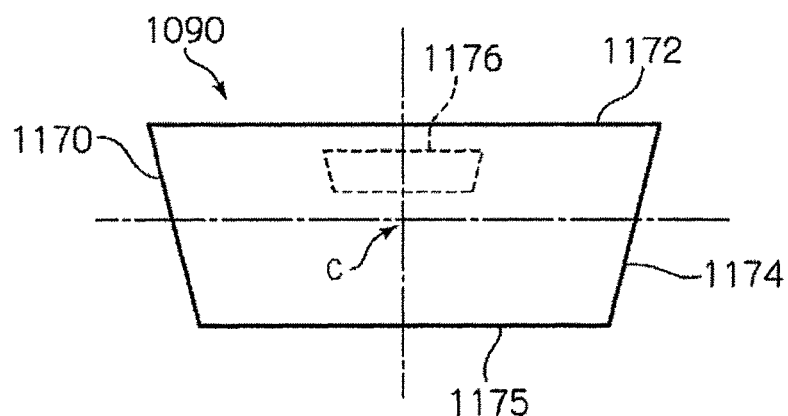
FIG. 12B illustrates another example of the relationship between the gate position and a sink mark.
Figure 12C:
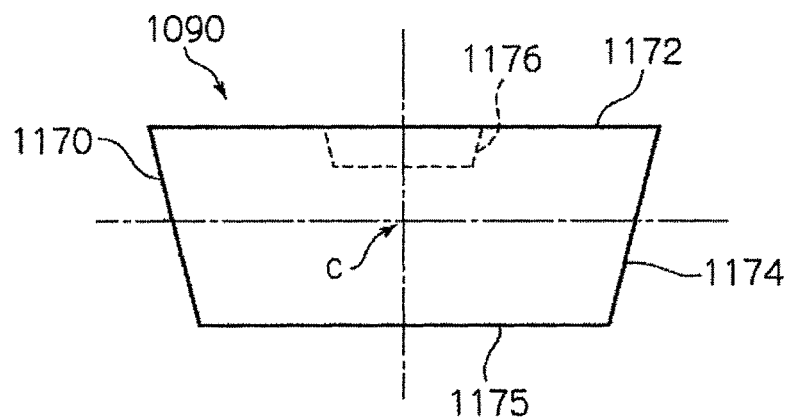
FIG. 12C illustrates another example of the relationship between the gate position and a sink mark.

FIG. 12A to FIG. 12C illustrate examples of the gate position that satisfies the above-described condition, i.e. being in the gate position area (within W). In a first example as illustrated in FIG. 12A, the gate 1176 is disposed on the side of the center C of the prism 1090 with respect to the thickness direction of the prism 1090. In a second example as illustrated in FIG. 12B, the gate 1176 is disposed in the middle between the center C of the prism 1090 and the reflection surface 1172 with respect to the thickness direction of the prism 1090. In a third example as illustrated in FIG. 12C, the gate 1176 is disposed on the reflection surface 1172 with respect to the thickness direction of the prism 1090.

When the prism 1090 is formed with the gate position as described above, the prism 1090 has such a volume balance with reference to the gate that the volume on the opposing surface 1175 side is greater with reference to the gate. This makes thermal shrinkage be caused mainly on the opposing surface 1175 side, which enables forming a sink mark preferentially in the opposing surface 1175.

Positional Relationship Between Prism Shape and Ejector Pins

Figure 13A:
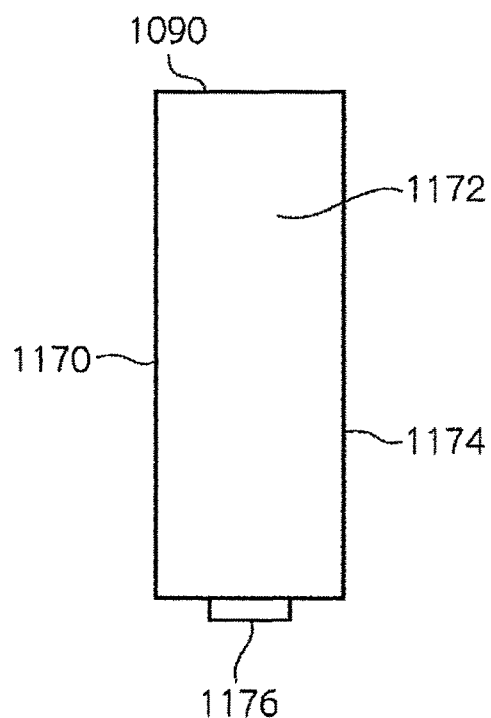
FIG. 13A is a plan view illustrating an example of the positional relationship between the shape of a prism and an ejector pin.
Figure 13B:
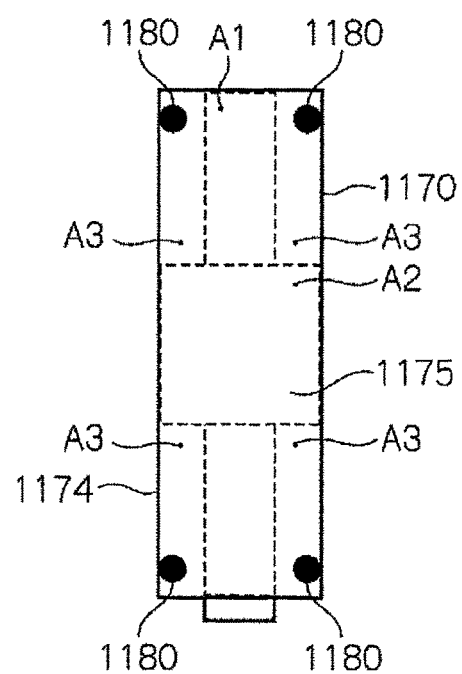
FIG. 13B is a bottom view of FIG. 13A.

It is required that the positional relationship between the shape of the prism 1090 and the marks 1180 of the ejector pins 1320 meets the following condition. The marks 1180 of the ejector pins 1320 in the prism 1090 are formed at the position where the ejector pins 1320 abut the prism 1090. As illustrated in FIG. 13B, the ejector pin marks 1180 are located in areas A3 that are the areas in the opposing surface 1175 excluding a first projection area (hereinafter referred to as a "gate extension area A1"), which is the projection on the opposing surface 1175 of a gate extension area A1 that is an extension of the gate 1176 in the longitudinal direction of the prism 1090 by a length equal to the prism 1090, and a second projection area (hereinafter referred to as an "excitation light passing area A2"), which is the projection on the opposing surface 1175 of the area where the excitation light EL passes through (see FIG. 13B, FIG. 14B and FIG. 15B). A plurality of ejector pins 1320 may be provided outside these areas, and the ejector pins 1320 are not limited in terms of the shape and the material. The longitudinal direction of the prism 1090 refers to the direction perpendicular to both the thickness direction and the width direction of the prism 1090.

In a first example as illustrated in FIG. 13B, the ejector pin marks 1180 are located in the areas A3 in the opposing surface 1175 that excludes the gate extension area A1, which is an extension of the gate 1176 in the longitudinal direction of the prism 1090 by a length equal to the prism 1090, and the excitation light passing area A2. Further, the marks 1180 of the ejector pins 1320 are arranged such that each of the four corners of the opposing surface 1175 (each of the areas A3) has one mark 1180.

Figure 14A:
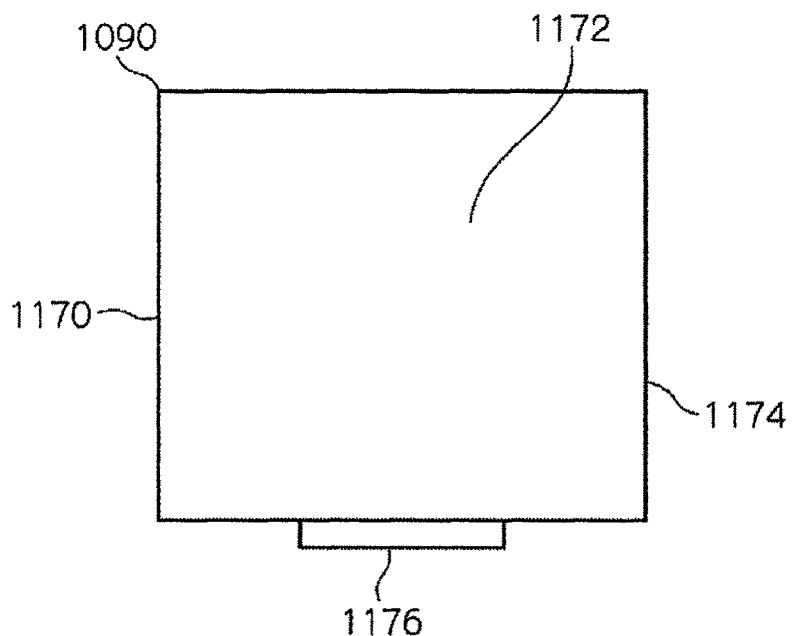
FIG. 14A is a plan view illustrating another example of the positional relationship between the shape of a prism and an ejector pin.
Figure 14B:
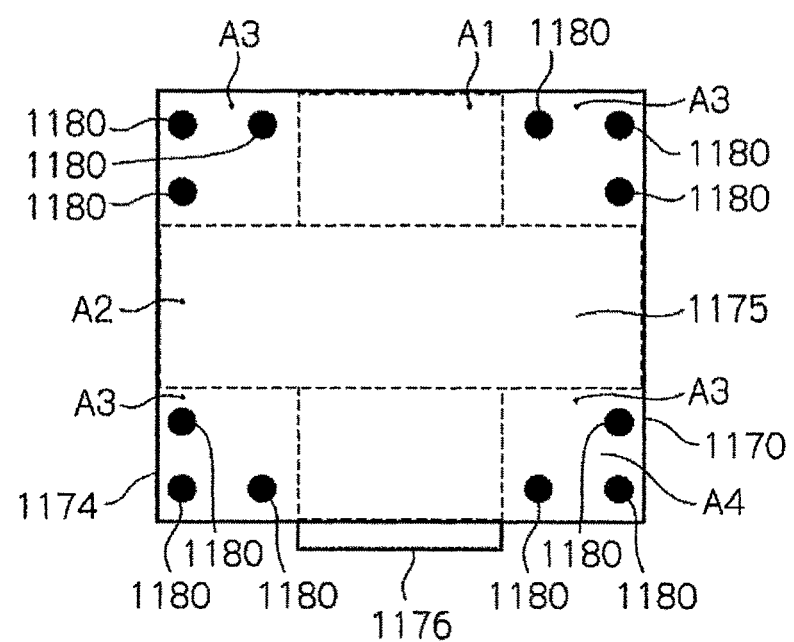
FIG. 14B is a bottom view of FIG. 14A.

In a second example as illustrated in FIG. 14B, the ejector pin marks 1180 are located in the area A3 in the opposing surface 1175 that exclude the gate extension area A1, which is an extension of the gate 1176 in the longitudinal direction of the prism 1090 by a length equal to the prism 1090, and the excitation light passing area A2. Further, the marks 1180 of the ejector pins 1320 are arranged such that each of the four corners of the opposing surface 1175 has three marks 1180.

Figure 15A:
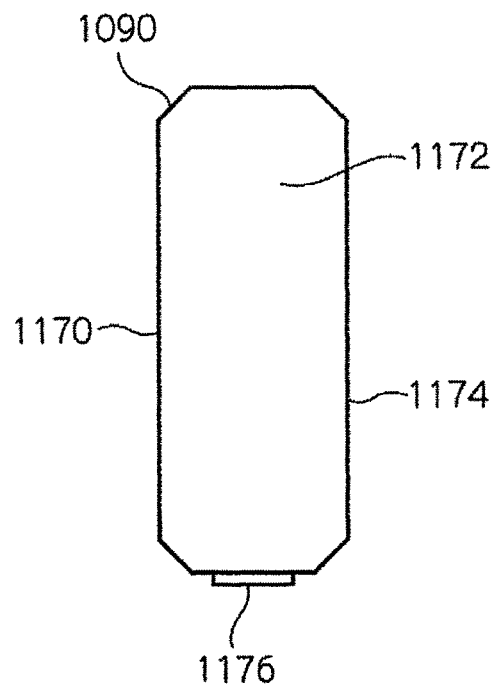
FIG. 15A is a plan view illustrating another example of the positional relationship between the shape of a prism and an ejector pin.
Figure 15B:
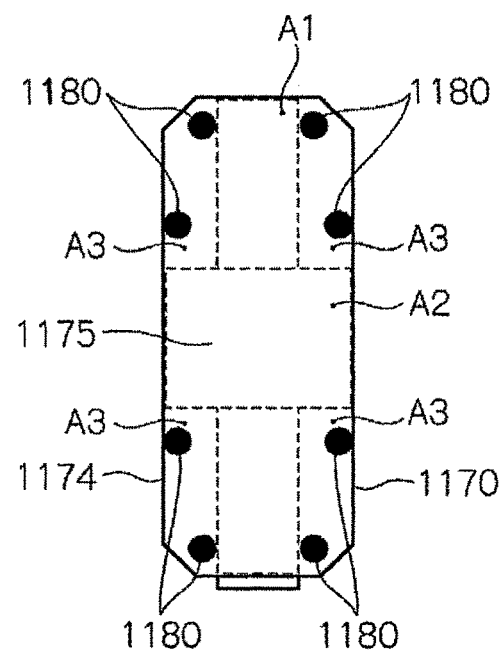
FIG. 15B is a bottom view of FIG. 15A.

In a third example as illustrated in FIG. 15B, the ejector pin marks 1180 are located in the area A3 in the opposing surface 1175 that exclude the gate extension area A1, which is an extension of the gate 1176 in the longitudinal direction of the prism 1090 by a length equal to the prism 1090, and the excitation light passing area A2. Further, the marks 1180 of the ejector pins 1320 are arranged such that each of the four corners of the opposing surface 1175 has two marks 1180.

The advantageous effects of the above-described configuration will be described later.

Relationship Between Ejecting Method and
P-Polarization Maintenance Ratio

Figure 16A:
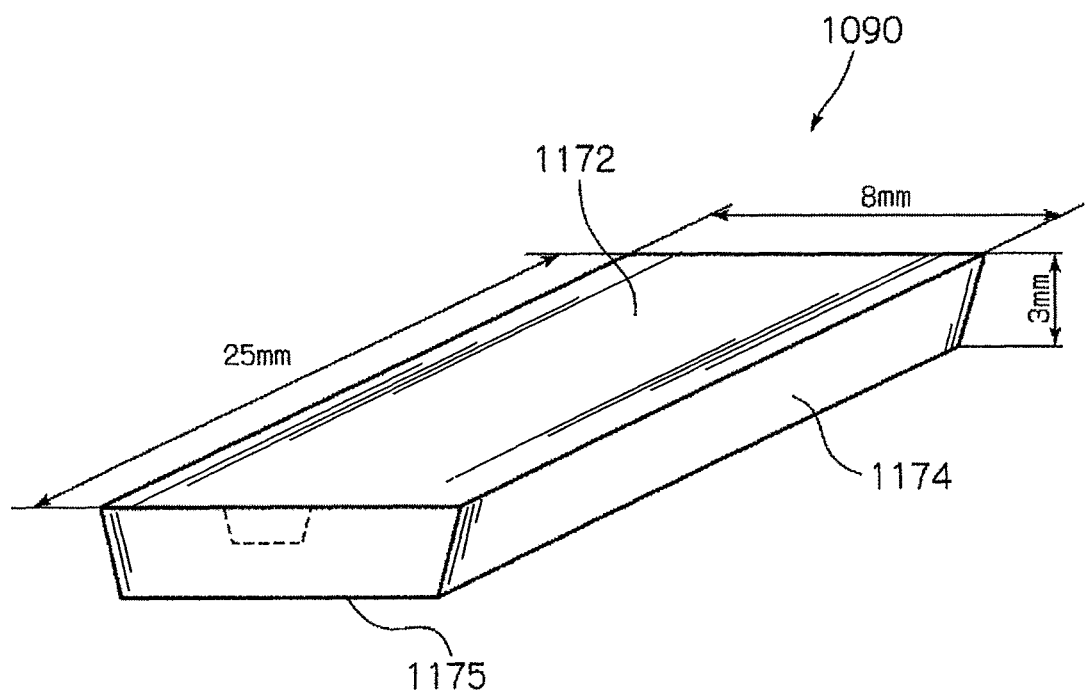
FIG. 16A is a perspective appearance view of a prism used for measurement.
Figure 16B:
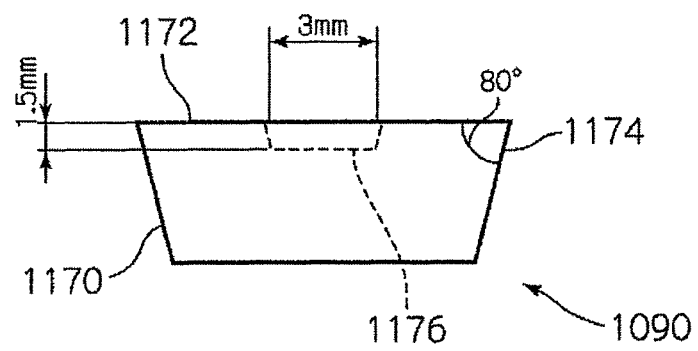
FIG. 16B is a vertical cross sectional view of FIG. 16A.
Figure 19:
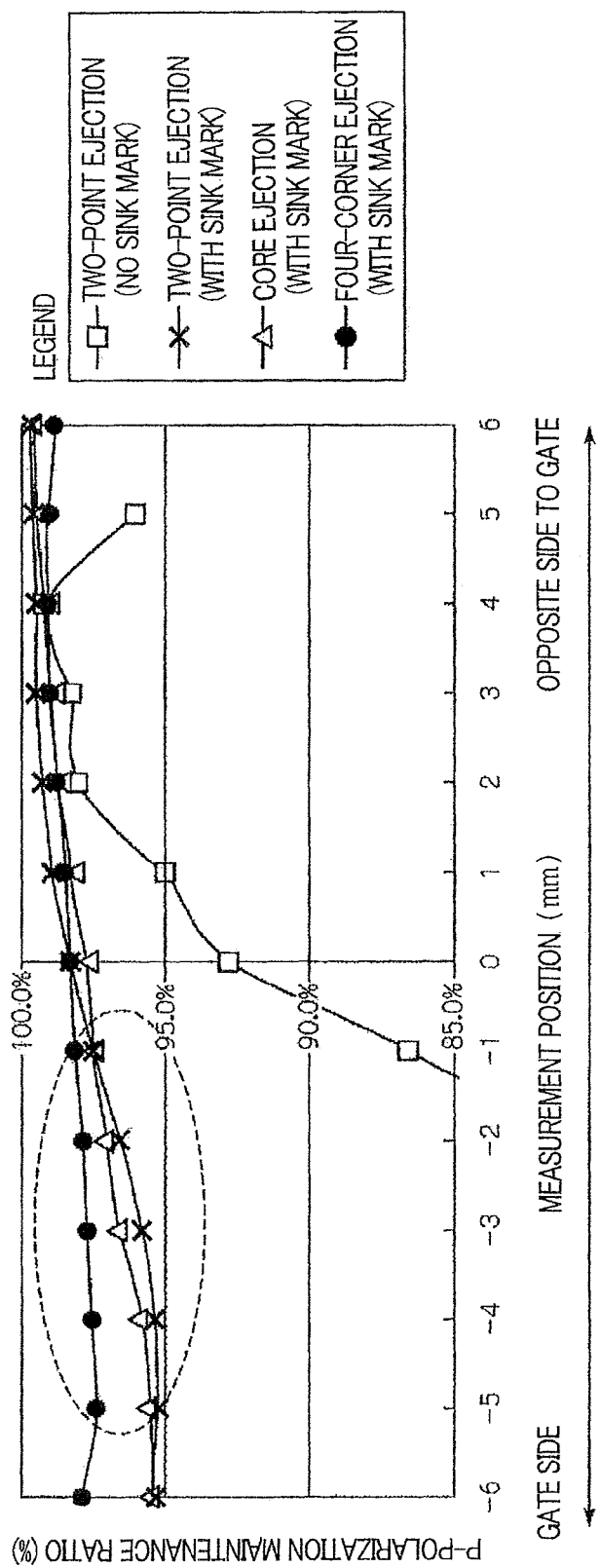
FIG. 19 is a graph of the distribution of P-polarization maintenance ratio with regard to presence/absence of a sink mark and different ejection techniques.

In the following, the relationship between the ejecting method, which is represented by the position of the ejector pins 1320 and the ejector pin marks 1180, and the distribution of the P-polarization maintenance ratio will be described along with the presence or absence of the sink-mark surface. In the examples, the trapezoidal prisms 1090 as illustrated in FIG. 16A and FIG. 16B (25 mm length, 8 mm width, 3 mm height, 80° inclination of side walls with respect to the reflection surface, 3 mm gate width and 1.5 mm gate thickness) are chosen as measuring objects. Regarding the measuring method, the P-polarization maintenance ratio (%) is measured in the above-described detection range in ±1 mm increments from the center. FIG. 19 shows the measurement results. The birefringence distribution is uniform in the gate side (see the area enclosed by a dashed line in FIG. 19).

Figure 18A:
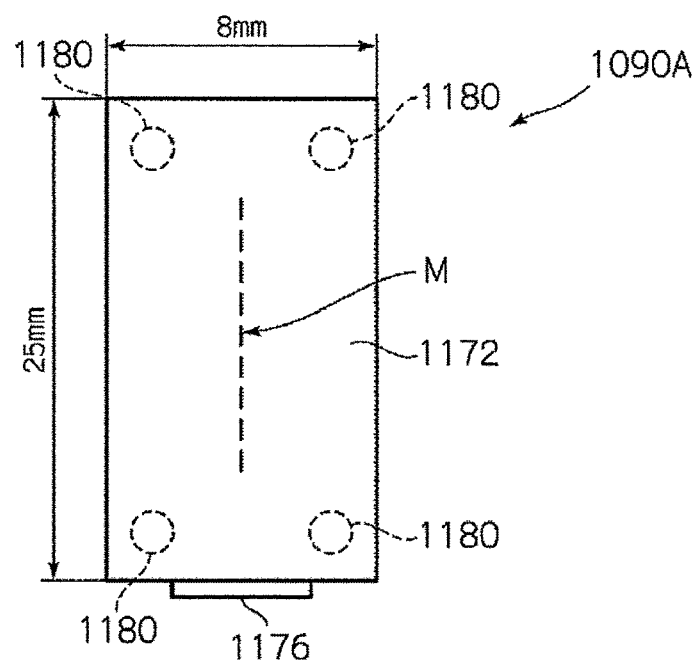
FIG. 18A is a plan view of a prism according to Example 3.
Figure 18B:
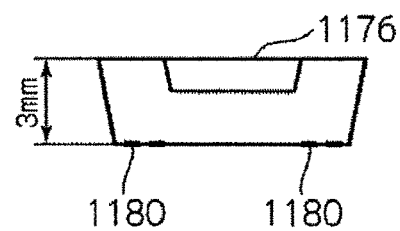
FIG. 18B is a vertical cross sectional view of FIG. 18A.
Figure 18C:
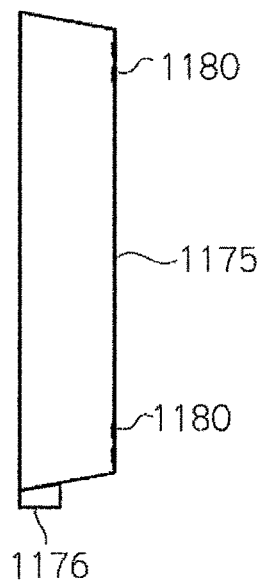
FIG. 18C is a side view of FIG. 18A.

The measuring objects are Comparison (two-point ejection, no sink mark) and inventive examples, Example 1 (two-point ejection, with sink mark), Example 2 (core ejection) and Example 3 (four-point ejection (four-corner ejection, with sink mark). As illustrated in FIG. 18A, a prism 1090A of Example 3 has ejector pin marks 1180 in the areas in the opposing surface that exclude the gate extension area, which is an extension of a gate 1176 in the longitudinal direction of the prism 1090 by a length equal to the prism 1090, and the excitation light passing area.

Figure 20A:
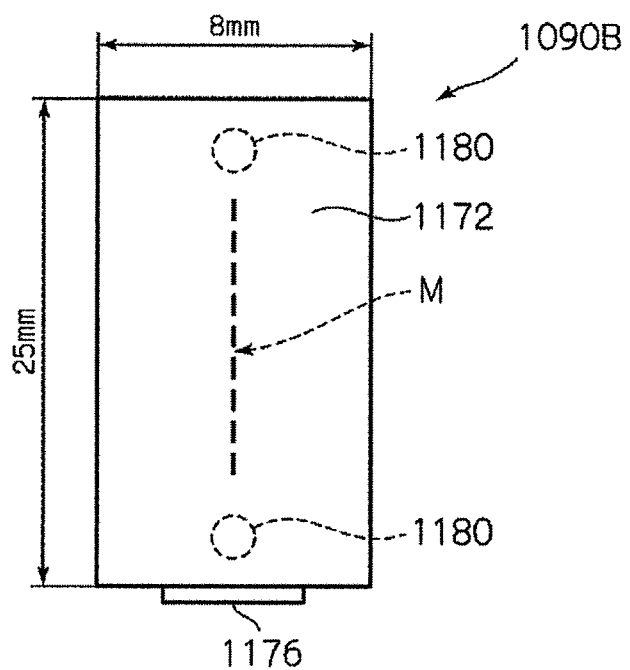
FIG. 20A is a plan view of a prism according to Comparison or Example 1.
Figure 20B:
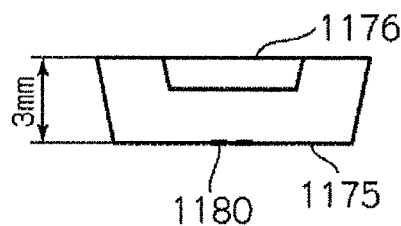
FIG. 20B is a vertical cross sectional view of FIG. 20A.
Figure 20C:
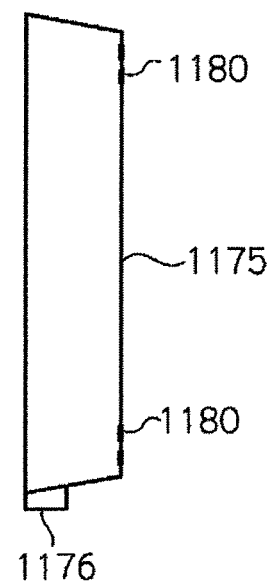
FIG. 20C is a side view of FIG. 20A.

As illustrated in FIG. 20A, a prism 1090B of Comparison has ejector pin marks 1180 in the area in the opposing surface that includes the gate extension area, which is an extension of a gate 1176 in the longitudinal direction of the prism 1090 by a length equal to the prism 1090, and excludes the excitation light passing area. The prism 1090B does not have a sink mark in an opposing surface.

Figure 21A:
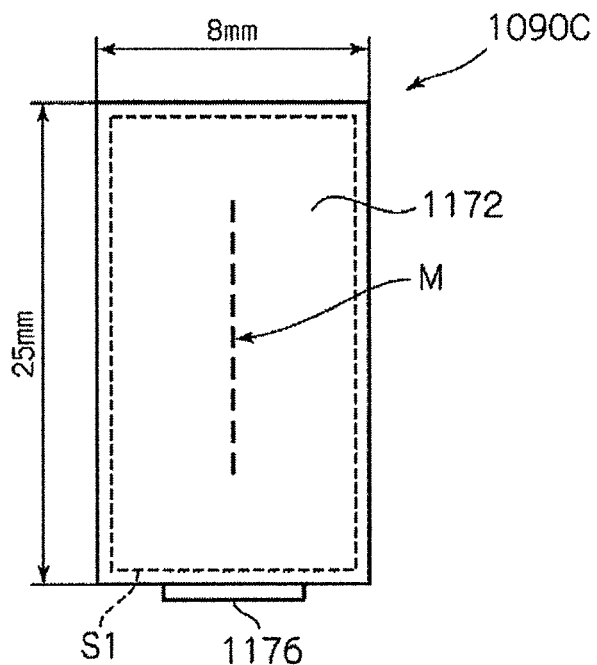
FIG. 21A is a plan view of a prism according to Example 2.
Figure 21B:
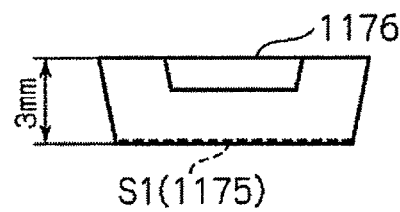
FIG. 21B is a vertical cross sectional view of FIG. 21A.
Figure 21C:
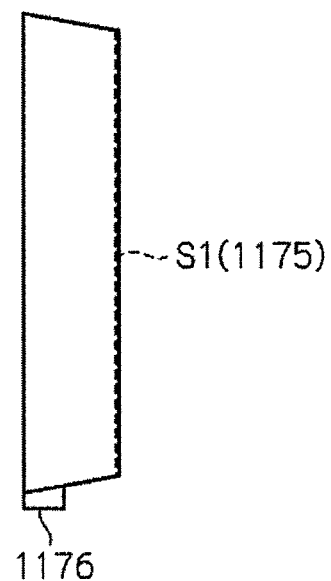
FIG. 21C is a side view of FIG. 21A.

A prism 1090B of Example 1 is the same as that of Comparison except that it has a sink mark in an opposing surface. As illustrated in FIG. 21A, a prism 1090C of Example 2 is molded by face ejection (S1 in FIG. 21A) by means of a core (not shown) and has a sink mark in an opposing surface 1175.

Figure 17A:
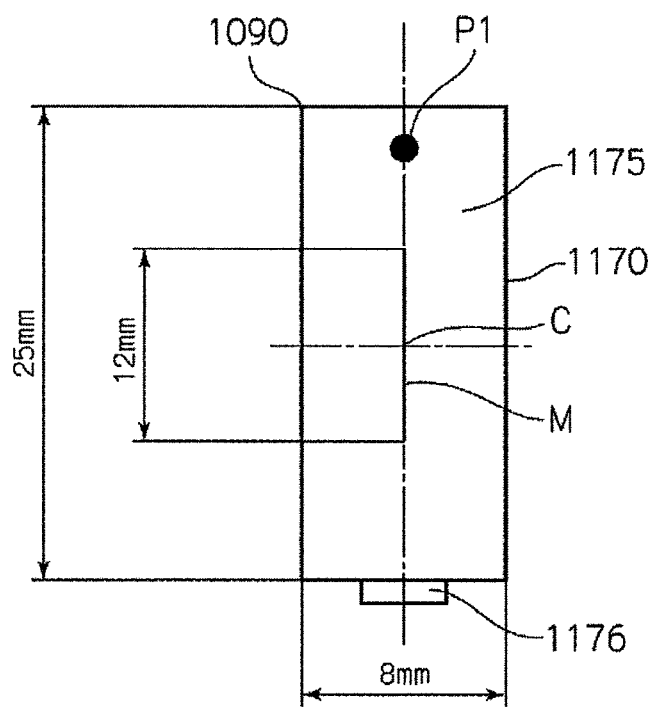
FIG. 17A is a plan view of a prism for illustrating measurement of the amount of sink mark.
Figure 17B:
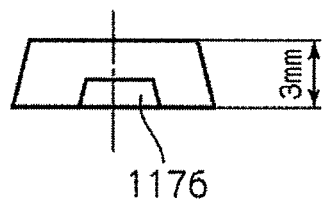
FIG. 17B is a vertical cross sectional view of FIG. 17A.

Measurement of the amount of sink mark will be briefly described referring to FIG. 17A and FIG. 17B.

Table 1 shows the results of measuring the amount of sink mark formed in the opposing surface in Comparison, Example 1, Example 2 and Example 3.

A height gauge is used for the measurement, and the height with respect to a measurement reference point P1 (where the height is zero) as illustrated in FIG. 17A is measured as the amount of sink mark. The measurement range M was set to ±6 mm in the longitudinal direction of the prism from the center C of the prism as illustrated in FIG. 17A. While the measurement range M is set to ±6 mm in the embodiment, it is not limited thereto.

The amount (height) of sink mark in Comparison is equal to or less than 3 μm. The amount (height) of sink mark in Example 1 is equal to or greater than 25 μm. The amount (height) of sink mark in Example 2 is equal to or greater than 25 μm. The amount (height) of sink mark in Example 3 is equal to or greater than 25 μm.

The shape and the outer dimension of the prisms and the gates used are as described above. Regarding the molding material, "ZEONEX_E48R" (trade name) is used as the resin material, and the prisms are produced according to the above-described "production method of prism".

When the maintenance ratio (P-polarization maintenance ratio) of the P-polarization component of the excitation light EL is equal to or greater than 90%, desirably equal to or greater than 96%, and the distribution of the maintenance ratio in a predetermined detection area (in the embodiment, ±6 mm in the longitudinal direction of the prism from the center of the reflection surface area of the prism 1090) is 95±5%, desirably 98±2%, the polarization maintenance ratio and the polarization condition can be regarded as high and uniform, and it is therefore possible to improve the sensitivity and the accuracy of measurement.

Looking at the measurement results in consideration of the above, it is found that Example 1, Example 2 and Example 3 exhibit a P-polarization maintenance ratio (%) of 90% or more over the entire measurement area. Further, it is found that Example 1 and Example 2 exhibit a P-polarization maintenance ratio (%) of 95% or more over the entire measurement area. Further, it is found that Example 3 exhibits a P-polarization maintenance ratio (%) of 96% or more and a distribution of the P-polarization maintenance ratio of 98±2% over the entire measurement area.

In a more detailed analysis, in Comparison, the P-polarization maintenance ratio is not 90% or more over the entire measurement area, and the distribution of the P-polarization maintenance ratio is not 98±2% either.

In Example 1, the P-polarization maintenance ratio is equal to or greater than 90% over the entire measurement area, but the distribution of the P-polarization maintenance

TABLE 1

| | FOR COMPARISON TWO-POINT EJECTION, WITH EJECTING MECHANISM ON EXTENSION OF GATE | EXAMPLE 1 TWO-POINT EJECTION, WITH EJECTING MECHANISM ON EXTENSION OF GATE | EXAMPLE 2 CORE EJECTION, WITH EJECTING MECHANISM ON EXTENSION OF GATE | EXAMPLE 3 FOUR-CORNER EJECTION, NO EJECTING MECHANISM ON EXTENSION OF GATE OR IN BEAM INCIDENT AREA |
|---|---|---|---|---|
| SINK MARK IN SINK-MARK SURFACE | NO (CONCAVE OF 3 μm OR LESS) | YES (CONCAVE OF 25 μm OR MORE) | YES (CONCAVE OF 25 μm OR MORE) | YES (CONCAVE OF 25 μm OR MORE) |
| P-POLARIZATION MAINTENANCE RATIO AND THE DISTRIBUTION THEREOF | X | ○ | ○ | ◎ | ratio is not 98±2%. In terms of whether the distribution is uniform or not, the distribution is uniform, but the area where the distribution is uniform is smaller than that of Example 3.

In Example 2, the P-polarization maintenance ratio is equal to or greater than 90% over the entire measurement area, but the distribution of the P-polarization maintenance ratio is not 98±2% as with Example 1. In terms of whether the distribution is uniform or not, the distribution is uniform, but the area where the distribution is uniform is smaller than that of Example 3.

In Example 3, the distribution is uniform over the entire measurement area.

Advantageous Effects

In view of the foregoing, the present invention can improve the sensitivity and the accuracy of measurement since it can be said that the polarization maintenance ratio and the distribution of the polarization condition are high and uniform.

That is, with the present invention, it is possible to cause a sink mark (form the sink-mark surface 1200) preferentially and stably in the opposing surface 1175 of the prism 1090 and also to equalize the distribution of the sink mark even when the prism is a dielectric resin prism. Therefore, it is possible to provide a resin prism for an analysis utilizing surface plasmon resonance at low cost, which has high polarization maintenance ratio and uniform distribution of polarization condition.

In particular, even when light is transmitted through the prism 1090 with the gold film 1092 in order to control the film thickness of the gold film 1092, the transmitted light is not diffused on the sink-mark surface 1200 since the sink-mark surface 1200 is transparent. Therefore, it is possible to measure the film thickness of the gold film 1092 without preparing a glass for monitoring the film thickness (see FIG. 3B). As a result, it is possible to accurately determine the actual film thickness of the gold film 1092 and thus to improve the sensitivity and the accuracy of the detection of a substance of interest.

In this regard, the film thickness of the gold film 1092 and the optical constants n (refractive index) and k (attenuation coefficient) can also be determined by means of an ellipsometer using ellipsometry known in the art (a technique of measuring a change of the polarization condition (incidence and reflection) when light is reflected on the surface of a substance and thereby obtaining information on the substance).

Regarding the positional relationship between the antigen trapping position of the gold film 1092 and the transparent sink mark (the sink-mark surface 1200) in the opposing surface 1175 opposed to the reflection surface 1172 of the prism 1090, it is more desirable that the transparent sink-mark surface 1200 is disposed vertically right below the area including the antigen trapping position of the gold film 1092, at least in the area where the light transmittance is measurable or in the area where an ellipsometer can be used for a measurement (e.g. approximately from 3 mm to 10 mm in width or diameter φ.

In more detail, the sink-mark surface 1200 is disposed on a straight line (perpendicular line) perpendicular to the gold film 1092 right below the area including the antigen trapping position of the gold film 1092. Further, the size of the sink-mark surface 1200 is larger than the size of said area including the antigen trapping position of the gold film 1092.

It is possible to readily produce high-precision SPR/SPFS analysis chips at low cost. Resin prisms available for SPR/SPFS analysis can be produced from a resin material that has a photoelastic coefficient of $80\lambda10^{-12}$ $Pa^{-1}$ or less or has a phase difference determined by Senarmont evaluation of 46 nm or more.

Figure 22:
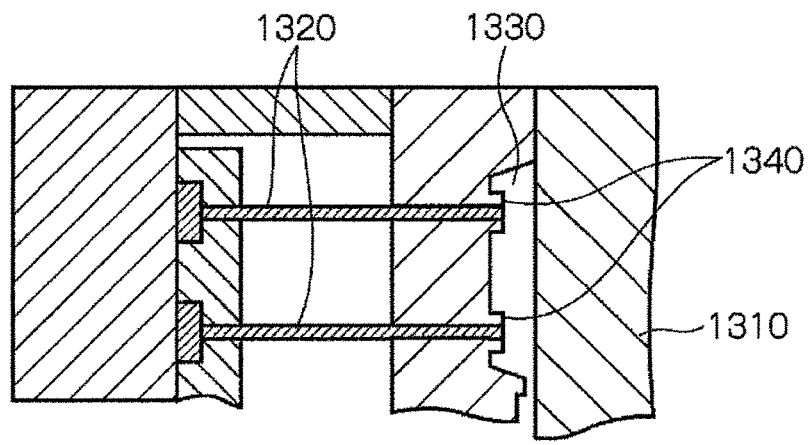
FIG. 22 is a schematic view of FIG. 10 in which a burr escape is further provided.
Figure 23A:
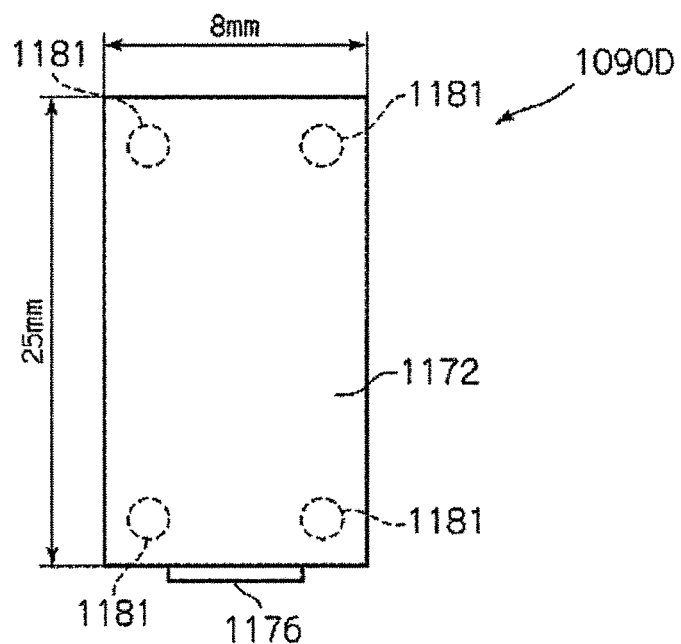
FIG. 23A is a plan view of a prism that is injection-molded by using the mold depicted in the schematic view of FIG. 10.
Figure 23B:
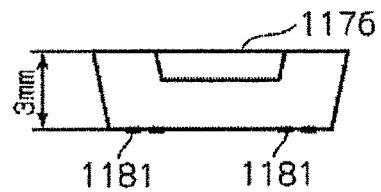
FIG. 23B is a vertical cross sectional view of FIG. 23A.
Figure 23C:
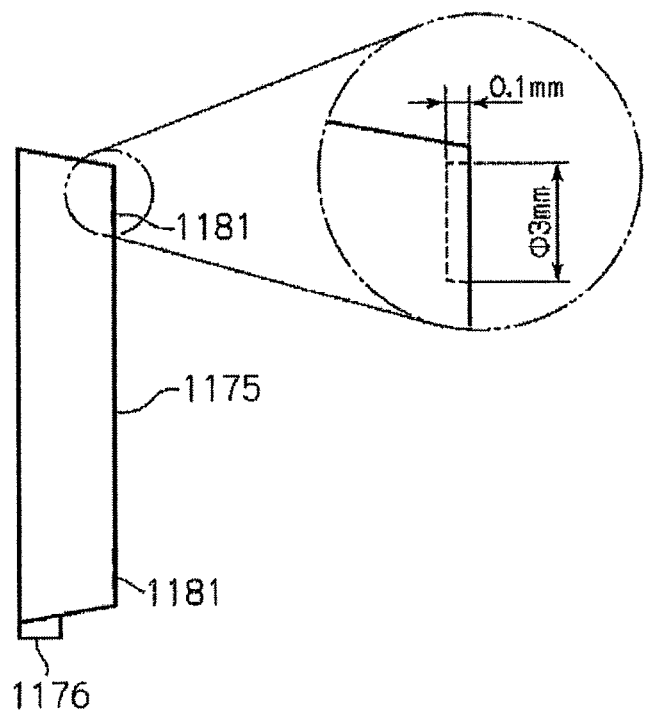
FIG. 23C is a side view of FIG. 23A.

Regarding the arrangement of the ejector pins, a burr escape is not provided in the examples of the present invention. However, when a burr should be avoided, a burr escape may be provided in the injection-molding mold, for example those denoted as 1340 in FIG. 22. FIG. 23A, FIG. 23B and FIG. 23C illustrate an example of the prism 1090D that is formed by using the injection-molding mold of FIG. 22 by a technique of four-point (four-corner) ejection. In FIG. 23B and FIG. 23C, 1181 denotes the transferred shape of the burr escapes 1340 in FIG. 22 on the prism 1090D.

While this invention is described in detail, the above description is merely exemplary in any sense, and the present invention is not limited thereto. A myriad of non-illustrated variations can be given without departing from the scope of this invention.

Second Embodiment

A second embodiment is different from the first embodiment in the following points.

Prism

Figure 24:
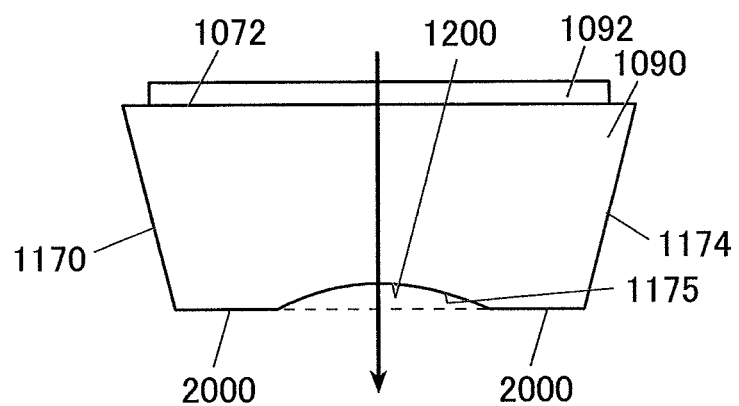
FIG. 24 is a side view of a prism according to a second embodiment.

As illustrated in FIG. 24, an opposing surface 1175 that is opposed to a reflection surface 1172 includes a sink-mark surface 1200 and non-sink-mark surfaces 2000. The sink-mark surface 1200 is provided at the center part of the opposing surface 1175, and the non-sink-mark surfaces 2000 are formed between the sink-mark surface 1200 and an incidence surface 1170 or an emission surface 1174. It is intended that a sink mark is not formed in the non-sink-mark surfaces 2000. The sink-mark surface 1200 and the non-sink-mark surfaces 2000 extend in the longitudinal direction of a prism 1090 in parallel to each other.

Mold

Figure 25A:
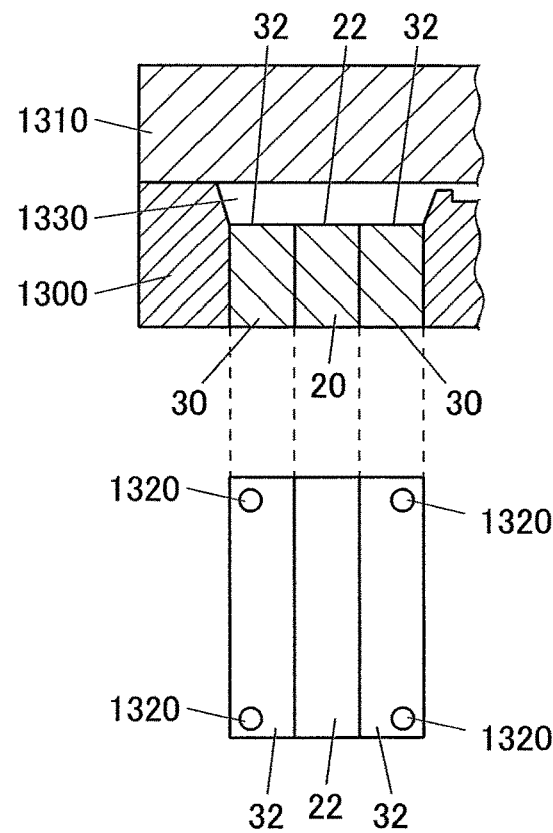
FIG. 25A is a partial enlargement of a movable mold according to the second embodiment, in which the upper part is a cross sectional view and the lower part is a plan view of a transfer area for forming a sink-mark surface.

As illustrated in FIG. 25A, the movable mold 1300 has a nest structure which includes a core 20 and cores 30. A transfer area 22 for forming the sink-mark surface 1200 is formed at the part of the core 20 that is exposed to the cavity, and transfer areas 32 for forming the non-sink-mark surfaces 2000 are formed at the parts of the cores 30 that are exposed to the cavity. The core 20 and the cores 30 extend in parallel to each other. They are arranged such that the core 20 is intervened between the cores 30. FIG. 25A illustrates an example in which ejector pins 1320 are disposed at the four corners of the cores 30.

In the configuration in FIG. 25A, since the transfer area 22 is a flat surface, the sink-mark surface 1200 that is formed by transferring the transfer area 22 is likely to be a concave surface. When the transfer area 22 has a flat surface, it is easier to process the mold surface (transfer area 22) and thus to adjust the surface roughness Ra of the transfer area 22 to within a range of 0.1 nm to less than 0.5 μm. Accordingly, it is possible to form the transparent sink-mark surface 1200.

Figure 25B:
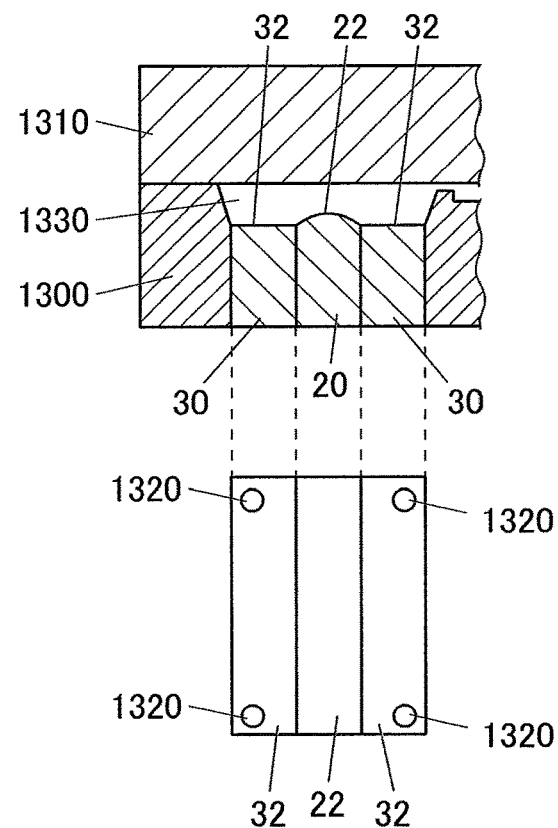
FIG. 25B illustrates a variation of FIG. 25A.
Figure 25C:
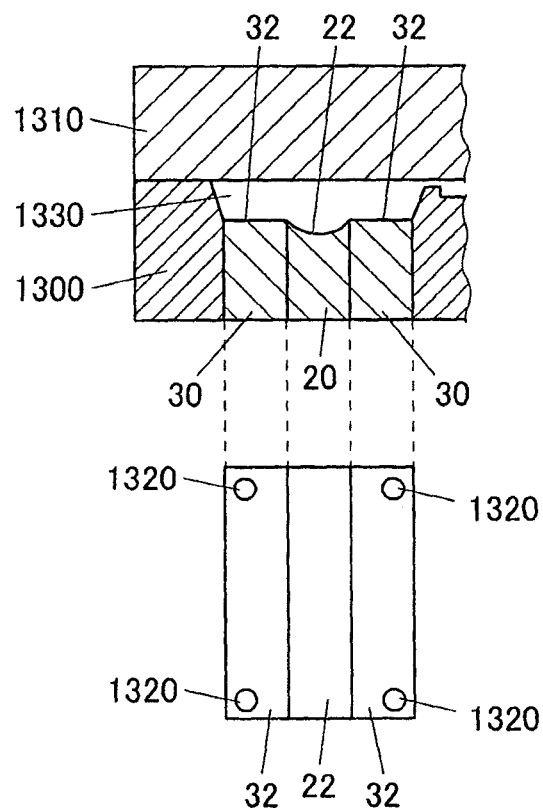
FIG. 25C illustrates a variation of FIG. 25A.
Figure 26:
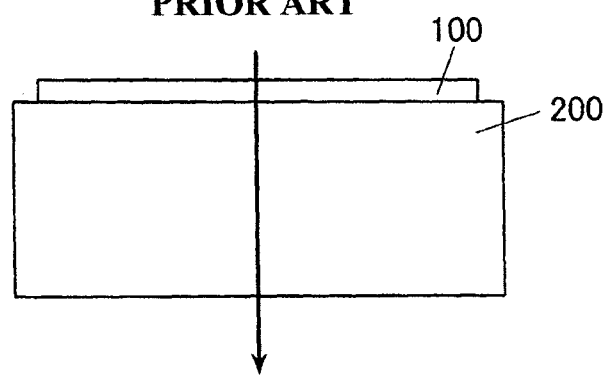
FIG. 26 illustrates a control of the film thickness of a metal film in the prior art.

As illustrated in FIG. 25B, the transfer area 22 of the core 20 may prospectively have a convex surface. Alternatively, as illustrated in FIG. 25C, the transfer area 22 of the core 20 may have a concave surface. Particularly with the configuration in FIG. 25C, it is possible to form the sink-mark surface 1200 into an approximately flat shape when a sink mark is formed in the sink-mark surface 1200 in resin molding. This enables the light transmittance to be readily measured.

Heat Conductivity (W·m/K)

The heat conductivity in the transfer area 22 of the core 20 is preferably from 0.6 W·m/K to 50 W·m/K, more preferably from 0.6 W·m/K to 20 W·m/K.

The heat conductivity in the transfer areas 32 of the cores 30 is preferably from 8 W·m/K to 200 W·m/K It is desirable that the heat conductivity in the transfer area 22 of the core 20 is less than the heat conductivity in the transfer areas 32 of the cores 30. This is because when the heat conductivity of the part to which a sink mark is intended to be accumulated is less than the heat conductivity of the part in which a sink mark is intended to be avoided, a sink mark does not expand to the optical surfaces (the incidence surface 1170 and the emission surface 1174) adjacent to the non-sink-mark surfaces 2000. This enables improving the surface accuracy of the optical surfaces.

Examples of mold materials that allow the heat conductivity in the transfer area 22 of the core 20 to fall within the preferred range include a SUS material pasted or coated with a heat insulating resin, a SUS material with a ceramic layer that is pasted thereto or laminated thereon by thermal spraying, a SUS material with an Ni—P plating laminated thereon, a titanium alloy, chromium alloy-based stainless steels such as STAVAX, prehardened steels such as HPM38 and NAK, carbon steel and the like.

The term "heat insulating resin" refers to a coating of polyimide, which is highly resistant to heat and chemical regents, or a film composed of a polyimide base and a heat resistant silicone adhesive is applied thereon. The "STAVAX" is a chromium alloy-based stainless steel that is particularly resistant to corrosion and abrasion. The STAVAX has a recommended HRC of approximately from 45 to 54, a density at ordinary temperature of 7800 kg/m$^3$ and a specific heat of 460 J/(kg·k), and contains Cr (chromium), V (vanadium), Mn (manganese), Si (silicon), C (carbon) and the like.

Examples of mold materials that allow the heat conductivity in the transfer areas 32 of the cores 30 to fall within the preferred range include copper alloys, aluminum alloys, titanium alloys, ultra-hard materials or ultra-hard materials with Ni—P plating or the like that imparts good processability, chromium alloy-based stainless steels such as STAVAX, prehardened steels such as HPM38 and NAK, carbon steel and the like.

Volume of Mold Material in Transfer Area for Forming Sink Mark

It is desirable that the thickness in the transfer area 22 of the core 20 is as thin as possible in order to avoid uneven cooling and to achieve stable and uniform distribution of birefringence. It should be understood well that the thickness is suitably adjusted according to the required specification of the prism 1090. For example, the configuration may be such that the base material is STAVAX, the entire surface of the transfer area 22 is uniformly plated with a low-heat conductive material, the transfer area 22 is lapped, and the end parts of the transfer area 22 are blasted so that the surface roughness Ra is greater in the end parts. Such configuration can induce a sink mark in the sink-mark surface 1200 and also reduce the influence of cracking on the optical surfaces (incidence surface 1170 and emission surface 1174) due to the blasted end parts with higher transferring property.

Surface Roughness Ra

The surface roughness Ra in the transfer area 22 of the core 20 is preferably from 0.1 nm to less than 0.5 µm. The "surface roughness Ra" represents arithmetic average roughness Ra according to JIS B 0601: 2013. Arithmetic average roughness Ra is principally the arithmetic average of absolute values of deviation from the average line to a measured curve in a zone that is extracted from the roughness curve and has a reference length in the direction of the average line. In arithmetic average roughness Ra, a single scratch (unevenness) has a very small influence on the measured value, and it is therefore possible to obtain a stable result.

In contrast, the surfaces in the transfer areas 32 of the cores 30 are processed by blasting, which are also referred to as grained surfaces. The surface roughness Ra of the grained surfaces (transfer areas 32 of the cores 30) is preferably from 0.5 µm to 100 µm.

For example, when the surface roughness Ra in the transfer area 22 of the core 20 is 0.1 nm, the surface is a so-called mirror surface that is finished by polishing, grinding or the like. A surface having a surface roughness Ra of less than 0.5 µm can be obtained by grinding and subsequent blasting with small particles that is also known as IEPCO processing.

The difference between the surface roughness Ra in the transfer area 22 of the core 20 and the surface roughness Ra in the transfer areas 32 of the cores 30 is preferably from 0.3 µm to less than 100 µm. This is because when the transfer area 22 of the core 20 has such a surface roughness Ra that does not affect the releasing step while the transfer areas 32 of the cores 30 have such a surface roughness that produces an anchor effect in the releasing step, the sink mark in the opposing surface 1175 does not expand to the adjacent optical surfaces (incidence surface 1170 and emission surface 1174), which can improve the surface accuracy of the optical surfaces.

The core 20 and the cores 30 are not necessarily separated from each other but may be formed integrally. In such cases, for example, an integral core may be made of STAVAX, which is processed into the respective surface shapes of the transfer areas 22, 32. Such processing methods include a method that involves graining (blasting) the entire core and subsequently mirror-finishing the area corresponding to the transfer area 22, a method that involves mirror-finishing the entire core and subsequently masking the area corresponding to the transfer area 22 and graining the areas corresponding to the transfer areas 32, and the like.

Also in this embodiment, the transparent sink-mark surface 1200 is formed in the opposing surface 1175 opposed to the reflection surface 1172 of the prism 1090. Therefore, in order to control the film thickness of the gold film 1092, it is possible to measure the film thickness of the gold film 1092 and thereby to accurately determine the actual film thickness of the gold film 1092 without preparing a glass for monitoring the film thickness (see FIG. 24).

Of course, the film thickness of the gold film 1092 and the optical constants n (refractive index) and k (attenuation coefficient) can also be determined by means of an ellipsometer using ellipsometry known in the art (a technique of measuring a change of the polarization condition (incidence and reflection) when light is reflected on the surface of a substance and thereby obtaining information on the substance).

Also in this embodiment, regarding the positional relationship between the antigen trapping position of the gold film 1092 and the transparent sink mark (the sink-mark surface 1200) in the opposing surface 1175 opposed to the reflection surface 1172 of the prism 1090, it is more desirable that the transparent sink-mark surface 1200 is disposed vertically right below an area including the antigen trapping position of the gold film 1092, at least in the area where the light transmittance is measurable or in the area where an ellipsometer can be used for a measurement (e.g. approximately from 3 mm to 10 mm in width or diameter φ).

In more detail, the sink-mark surface 1200 is disposed on a straight line (perpendicular line) perpendicular to the gold film 1092 right below said area including the antigen trapping position of the gold film 1092. Further, the size of the sink-mark surface 1200 is larger than the size of said area including the antigen trapping position of the gold film 1092.

INDUSTRIAL APPLICABILITY

The present invention is mainly applied to prisms that are used for an analysis utilizing surface plasmon, and is particularly suitably applicable for determining the accurate film thickness of a metal film formed on such prisms.

REFERENCE SIGNS LIST

1026 sensor chip
1090 prism
1092 gold film
1096 channel forming body
1170 incidence surface
1172 reflection surface
1174 emission surface
1175 opposing surface
1200 sink-mark surface
2000 non-sink-mark surface

The invention claimed is:

1. A prism which is constituted by a dielectric medium and is used for an analysis utilizing surface plasmon, comprising:
   an incidence surface through which excitation light enters from an outside;
   a reflection surface on which the excitation light which has entered through the incidence surface is reflected;
   an emission surface through which the excitation light which has been reflected on the reflection surface exits; and
   an opposing surface which is opposed to the reflection surface,
   wherein a metal film is formed on the reflection surface,
   wherein the opposing surface comprises a sink-mark surface,
   wherein the sink-mark surface is transparent,
   wherein a surface roughness Ra of the sink-mark surface is from 0.1 nm to less than 0.5 μm, and
   wherein the sink-mark surface comprises a curved surface which forms a convexity towards the reflection surface.

2. The prism according to claim 1,
   wherein the sink-mark surface is disposed vertically right below an area including an antigen trapping position of the metal film.

3. A method for producing the prism according to claim 1, comprising:
   preparing a mold with a certain cavity;
   injecting a certain resin to fill the cavity;
   applying a dwell pressure to the resin; and
   cooling the resin,
   wherein the mold comprises a transfer area for forming the sink-mark surface, and
   wherein a surface roughness Ra of the transfer area is from 0.1 nm to less than 0.5 μm.

4. A method for producing the prism according to claim 1, comprising:
   preparing a mold with a certain cavity;
   injecting a certain resin to fill the cavity;
   applying a dwell pressure to the resin; and
   cooling the resin,
   wherein the opposing surface of the mold comprises a first transfer area for forming the sink-mark surface and a second transfer area for forming a non-sink-mark surface between the sink-mark surface and the incidence surface or the emission surface,
   wherein a surface roughness Ra of the first transfer area is from 0.1 nm to less than 0.5 μm, and
   wherein a surface roughness Ra of the second transfer area is from 0.5 μm to less than 100 μm.

5. A mold for producing the prism according to claim 1, comprising:
   a transfer area for forming the sink-mark surface,
   wherein a surface roughness Ra of the transfer area is from 0.1 nm to less than 0.5 μm.

6. A mold for producing the prism according to claim 1, comprising:
   a first transfer area for forming the sink-mark surface of the opposing surface and a second transfer area for forming a non-sink-mark surface of the opposing surface between the sink-mark surface and the incidence surface or the emission surface,
   wherein a surface roughness Ra of the first transfer area is from 0.1 nm to less than 0.5 μm, and
   wherein a surface roughness Ra of the second transfer area is from 0.5 μm to less than 100 μm.

7. A sensor chip, comprising:
   the prism according to claim 1; and
   a channel forming body in which a channel is formed.

8. The prism according to claim 1, wherein the metal film is made of Gold.

9. The prism according to claim 8, wherein the Gold film has a film thickness of from 40 nm to 50 nm.

10. The prism according to claim 9, wherein the prism is made of a resin material comprising a cycloolefin polymer.

11. The prism according to claim 10, wherein water absorption of the prism is equal to or less than 0.2%.

12. The prism according to claim 11, wherein the resin material of the prism has a photoelastic coefficient equal to or less than $80 \times 10^{-12}$ Pa$^{-1}$.

* * * * *